US009597362B2

(12) United States Patent
Ross et al.

(10) Patent No.: US 9,597,362 B2
(45) Date of Patent: Mar. 21, 2017

(54) USE OF PROBIOTIC BACTERIA IN THE TREATMENT OF INFECTION

(75) Inventors: Paul Ross, Cork (IE); Stephen Hallahan, Dublin (IE); Colin Hill, Cork (IE); William Meaney, Cork (IE)

(73) Assignees: TEAGASC, THE AGRICULTURE AND FOOD DEVELOPMENT AUTHORITY, Dublin (IE); UNIVERSITY COLLEGE, CORK-NATIONAL UNIVERSITY OF IRELAND, Cork (IE)

( * ) Notice: Subject to any disclaimer, the term of this patent is extended or adjusted under 35 U.S.C. 154(b) by 2429 days.

(21) Appl. No.: 10/576,010

(22) PCT Filed: Oct. 15, 2004
(Under 37 CFR 1.47)

(86) PCT No.: PCT/IE2004/000143
§ 371 (c)(1),
(2), (4) Date: Aug. 6, 2007

(87) PCT Pub. No.: WO2005/034970
PCT Pub. Date: Apr. 21, 2005

(65) Prior Publication Data
US 2008/0233091 A1    Sep. 25, 2008

(30) Foreign Application Priority Data
Oct. 17, 2003 (IE) .................................... 2003/0773

(51) Int. Cl.
*A61K 35/744* (2015.01)
(52) U.S. Cl.
CPC .................................. *A61K 35/744* (2013.01)
(58) Field of Classification Search
CPC .............. A61K 2300/00; A61K 38/164; A61K 31/165; A61K 31/335; A61K 31/43; A61K 31/495; A61K 31/58; A61K 31/7028; A61K 31/7036; A61K 39/085; A61K 2039/55505; A61K 2039/523; A61K 2039/55522; A61K 2039/6037; A61K 31/395; A61K 31/702; A61K 31/715; A61K 31/7016; A61K 35/747; A61K 35/745; A61K 35/742; A61K 35/744; A61K 38/00; A61K 8/64; A61K 38/47; A23V 2002/00; A23V 2200/3202; A23V 2200/3204; A23V 2250/28; A23V 2200/32; A23V 2250/21166; A23V 2250/64; A23C 19/0323; A23C 19/11; A23L 3/34635; A61Q 11/00; A61Q 19/00; C07K 14/315; C07K 16/1271; C07K 2317/24; C07K 2317/33; C07K 2317/565; C07K 2317/569; C07K 2317/76; C07K 14/31; C07K 14/36; C12N 9/503; G01N 33/5023
See application file for complete search history.

(56) References Cited

U.S. PATENT DOCUMENTS

| | | | |
|---|---|---|---|
| 5,756,665 A * | 5/1998 | Mollet et al. | 530/326 |
| 5,804,179 A | 9/1998 | Reid et al. | |
| 5,965,128 A * | 10/1999 | Doyle et al. | 424/93.48 |
| 6,207,411 B1 * | 3/2001 | Ross et al. | 435/69.1 |
| 7,125,708 B2 * | 10/2006 | Wynne et al. | 435/252.9 |
| 7,589,250 B2 * | 9/2009 | Drevik et al. | 604/378 |
| 2002/0159976 A1 * | 10/2002 | Glenn et al. | 424/93.2 |

FOREIGN PATENT DOCUMENTS

| | | | |
|---|---|---|---|
| WO | WO 9632482 | * | 10/1996 |
| WO | WO 96/38159 | | 12/1996 |

OTHER PUBLICATIONS

Choi et al, "Production of a nisin-like bacteriocin by *Lactococcus lactis* subsp. *lactis* A164 isolated from Kimchi", J. of App. Microbio. pub year 2000, vol. 88, pp. 563-571.*
Twomey DP et al:, "Protection against *Stapylococcus aureus* Mastitis in dairy cows using a Bismuth-based teat seal containing the bacteriocin, lacticin 3147" Journal of Dairy Science, XX, US, vol. 83, No. 9, Sep. 2000, pp. 1981-1988, XP002189812 ISSN: 0022-0302.
Heikkila M P et al:, "Inhibition of *Staphylococcus aureus* by the Commensal Bacteria of Human Milk", Journal of Applied Microbiology, vol. 95, No. 3, 2003, pp. 471-478, XP002312462 ISSN: 1364-5072 Absracttables 1,2.
Database WPI, Section CH, Week 200381 Derwent Publications Ltd., London, GB; Class B04, AN 2003-869105 XP002312464 & JP 2003 259860 A (Zeng M J) Sep. 16, 2003 Abstract.
Alvarez-Olmos M I et al:, "Probiotic Agents and Infectious Diseases: A Modern Perspective on a Traditional Therapy", Clinical Infectious Diseases, The University of Chicago Press, Chicago, IL, US, vol. 32, Jun. 1, 2001, Pages ISSN: 1058-4838 the Whole Document.
Cross Martin L:, Microbes Versus Microbes: Immune Signals Generated by Probiotic Lactobicilli and Their Role in Protection, Against Microbial Pathogens. FEMS Immunology and Medical Microbiology, vol. 34, No. 4, Dec. 13, 2002, pp. 245-253, XP002312463 ISSN: 0928-8244 the Whole Document.
Kim Ji Yeon et al: "Screening for Antiproliferative Effects of Cellular Components From Lactic Acid Bacteria Against Human Cancer Cell Lines", Biotechnology Letters, vol. 24, No. 17 Sep. 2002, pp. 1431-1436, XP009042191 ISSN: 0141-5492 the Whole Document.
Parente et al.:, "A Comparison of Factors Affecting the Production of Two Bacterjocins From Lactic Acid Bacteria", Journal of Applied Bacteriology, vol. 73, No. 4, 1992, pp. 290-298, XP009042198 ISSN: 0021-8847 the Whole Document.

* cited by examiner

*Primary Examiner* — Debbie K Ware
(74) *Attorney, Agent, or Firm* — Young & Thompson

(57) ABSTRACT

The disclosure relates to the live cultures of probiotic bacteria to treat infectious diseases in humans and animals. Food-grade or non-pathogenic cultures are used to treat localised infections.

3 Claims, 18 Drawing Sheets

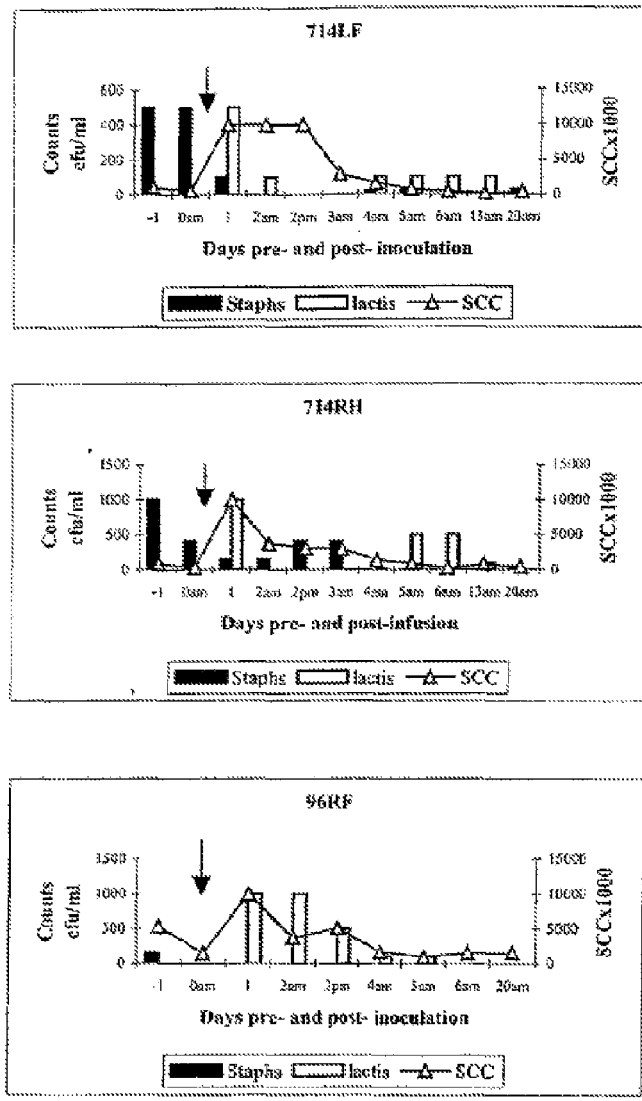

Figure 1A. Somatic Cell Count values and bacterial counts in quarters 714RH, 714LF and 96RF. The black arrow depicts the time of infusion. A clinical response was arbitrarily given a value of 10000 x 1000 SCC ml$^{-1}$. Bacterial counts are expressed as cfu ml$^{-1}$. When less than 400 bacteria ml$^{-1}$ were present, bacteria were counted precisely. Values greater than this were assigned an arbitrary value of 500 or 1000 (when the bacteria were too numerous to count) bacteria ml$^{-1}$.

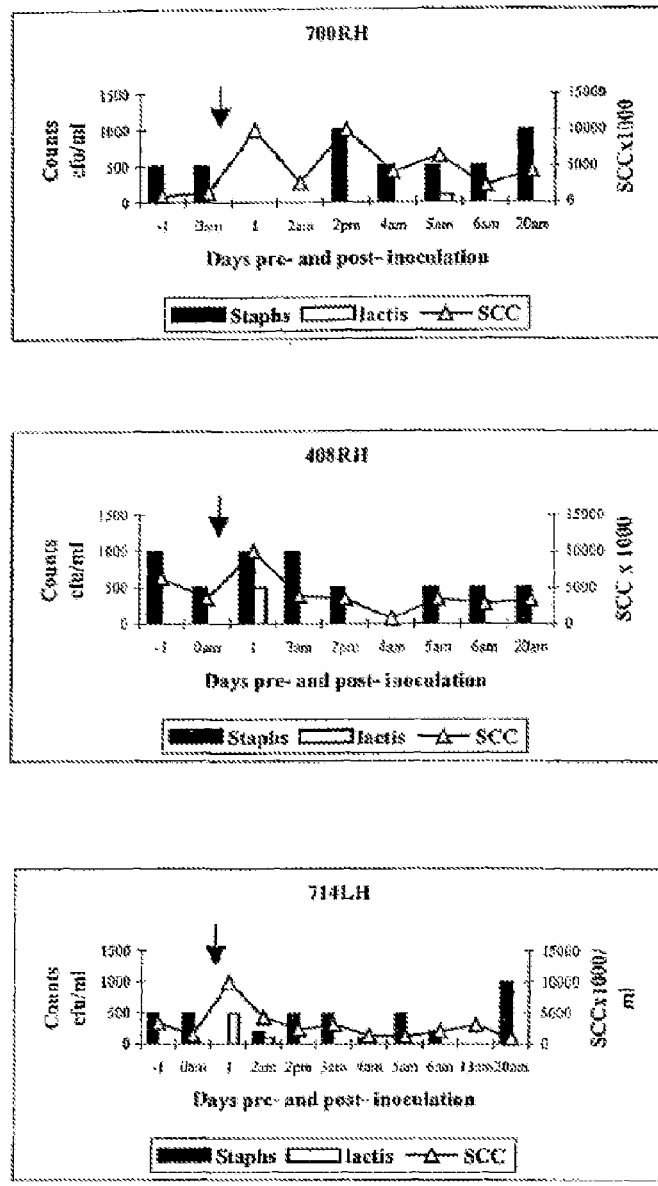

Figure 1B. Somatic Cell Count values and bacterial counts in quarters 700RH, 408RH and 714LH. The black arrow depicts the time of infusion. A clinical response was arbitrarily given a value of 10000 × 1000 SCC ml$^{-1}$. Bacterial counts are expressed as cfu ml$^{-1}$. When less than 400 bacteria ml$^{-1}$ were present, bacteria were counted precisely. Values greater than this were assigned an arbitrary value of 500 or 1000 (when the bacteria were too numerous to count) bacteria ml$^{-1}$.

Cow 1154LF. Milk sampled pre-infusion (left) and post-infusion (right).
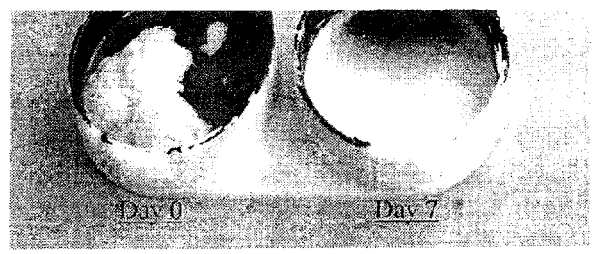
Figure 2A. Appearance of milk from Cow 1154LF sampled pre- and post-infusion of *Lactococcus lactis* DPC 3147. Samples shown on Day 0 and 7 days post-infusion.
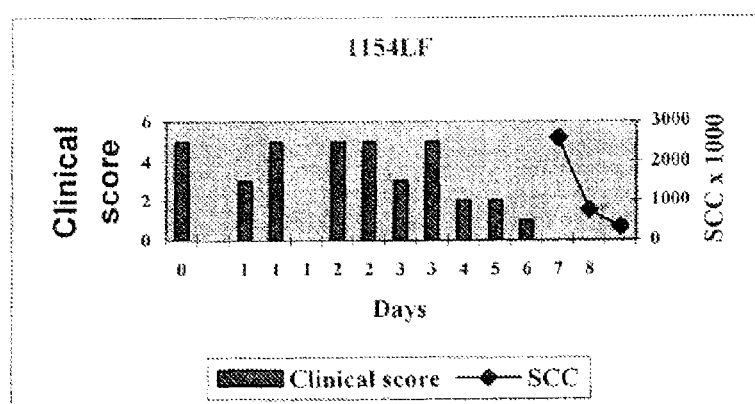
Figure 2B. Graphs of Somatic Cell Count and Clinical Score in milk from Cow 1154LF sampled pre- and post-infusion of *L. lactis* DPC 3147.

Cow 1178LH pre- (Day 0) and post- (Day 7) infusion.
Figure 3A. Appearance of milk from Cow 1178LH sampled pre- and post-infusion of *Lactococcus lactis* DPC 3147. Samples shown on Day 0 and 7 days post-infusion.
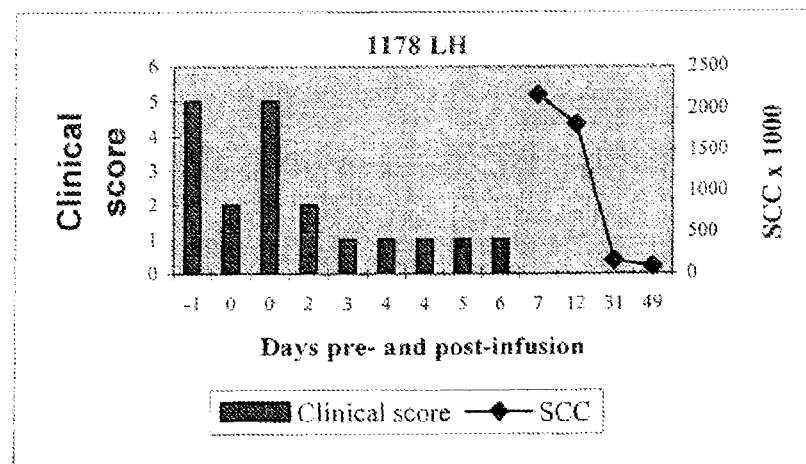
Figure 3B. Graphs of Somatic Cell Count and Clinical Score in milk from Cow 1178LH sampled pre-and post-infusion of *L. lactis* DPC3147.

Cow 1850RF pre- (Day 0) and post- (Day 9) infusion.
Figure 4A. Appearance of milk from Cow 1850RF sampled pre- and post-infusion of *Lactococcus lactis* DPC 3147. Samples shown on Day 0 and 9 days post-infusion.
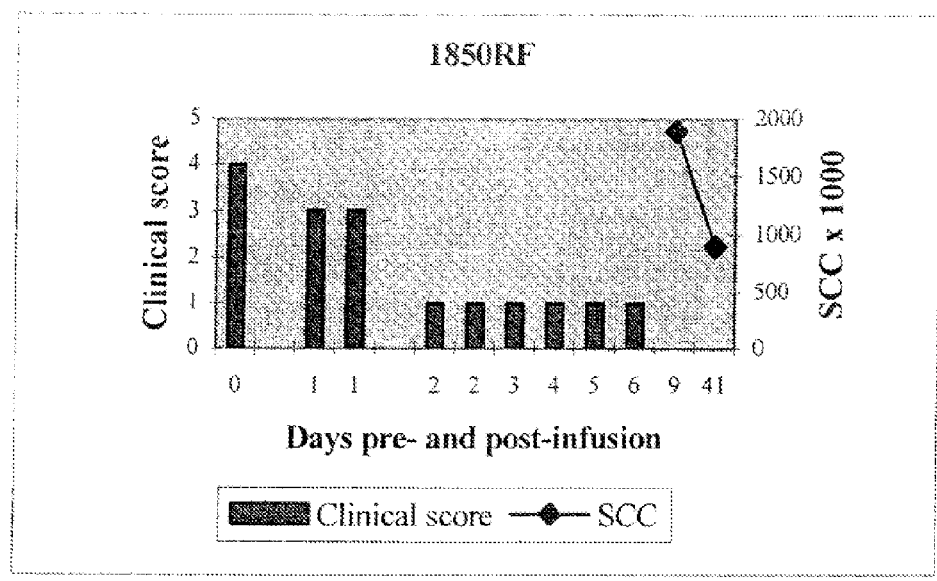
Figure 4B. Graphs of Somatic Cell Count and Clinical Score in milk from Cow 1850RF sampled pre- and post-infusion of *L. lactis* DPC 3147.

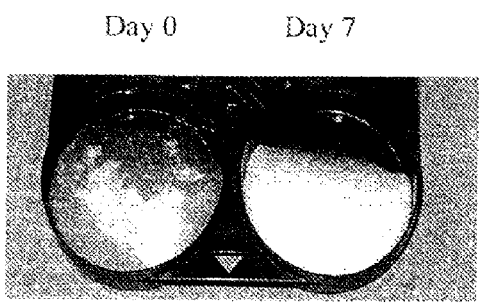
Figure 5A. Appearance of milk from Cow 1163RH sampled pre- and post-infusion of *Lactococcus lactis* DPC 3147. Samples shown on Day 0 and 7 days post-infusion.
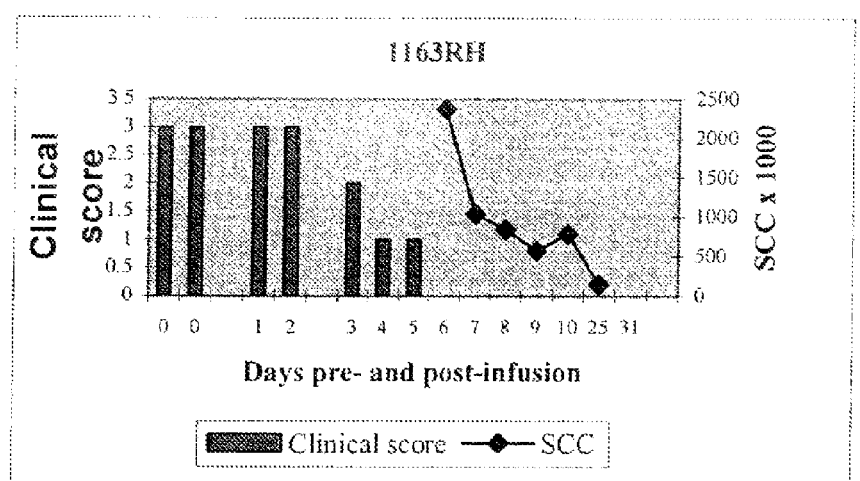
Figure 5B. Graphs of Somatic Cell Count and Clinical Score in milk from Cow 1163RH sampled pre- and post-infusion of *L. lactis* DPC 3147.

Cow 1184RF pre- (Day 0) and post- (day 6) infusion.
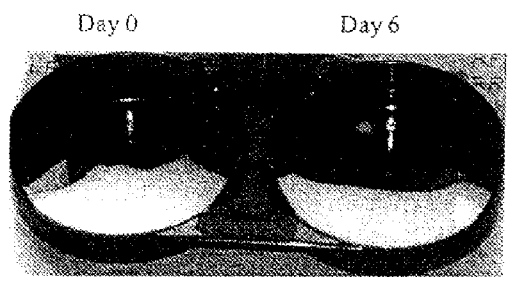
Figure 6A. Appearance of milk from Cow 1184RF sampled pre- and post-infusion of *Lactococcus lactis* DPC 3147. Samples shown on Day 0 and 6 days post-infusion.
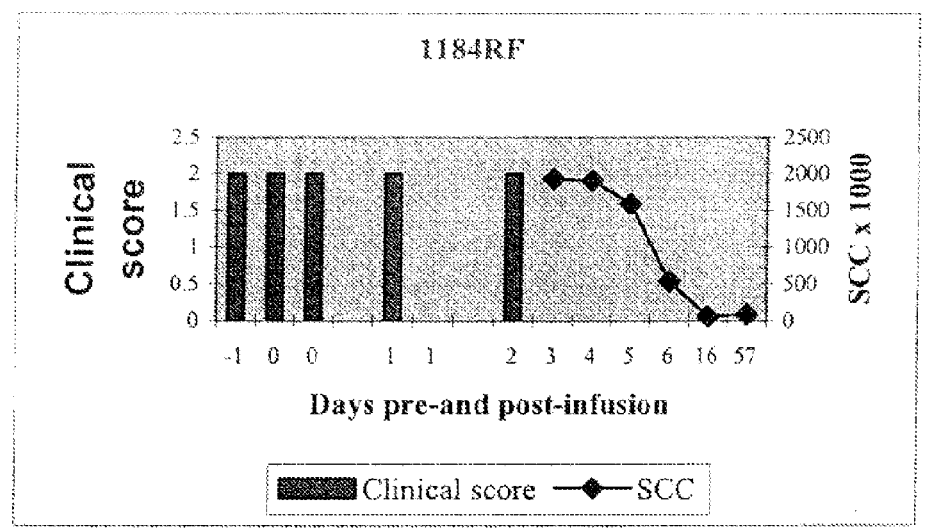
Figure 6B. Graphs of Somatic Cell Count and Clinical Score in milk from Cow 1184RF sampled pre- and post-infusion of *L. lactis* DPC 3147.

Cow 14LH pre- (Day 0) and post- (Day 7) infusion
Day 0                    Day 7
Figure 7A. Appearance of milk from Cow 14LH sampled pre- and post-infusion of *Lactococcus lactis* DPC 3147. Samples shown on Day 0 and 7 days post-infusion.
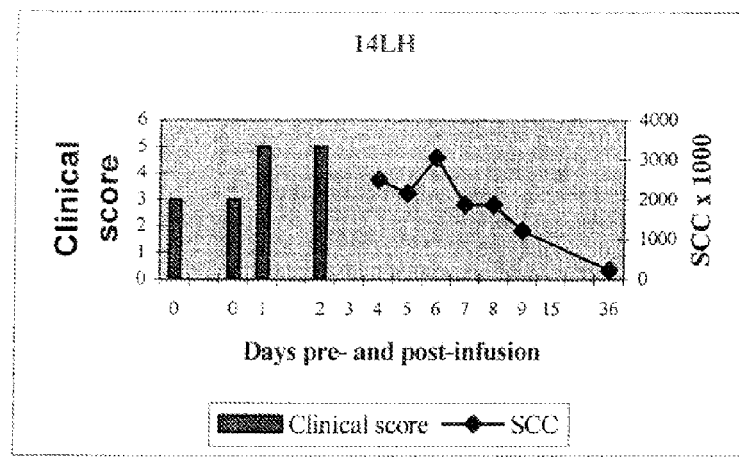
Figure 7B. Graphs of Somatic Cell Count and Clinical Score in milk from Cow 14LH sampled pre- and post-infusion of *L. lactis* DPC 3147.

Cow 717RF pre- (day 0) and post- (Day 7) infusion
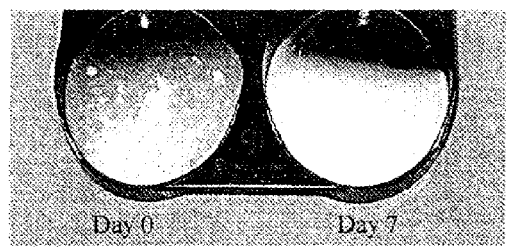
Figure 8A. Appearance of milk from Cow 717RF sampled pre- and post-infusion of *Lactococcus lactis* DPC 3147. Samples shown on Day 0 and 7 days post-infusion.
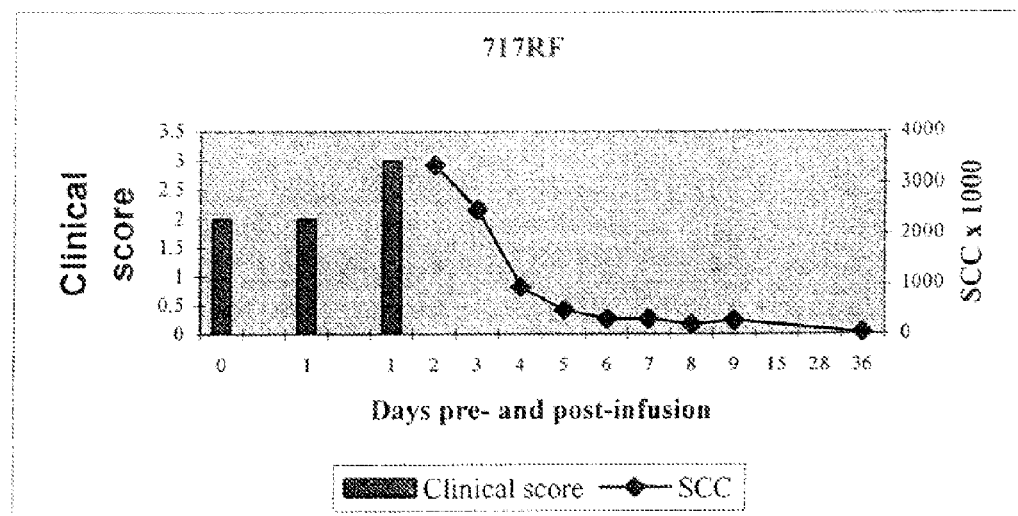
Figure 8B. Graphs of Somatic Cell Count and Clinical Score in milk from Cow 717RF sampled pre- and post-infusion of *L. lactis* DPC 3147.

Cow 264LF pre- (day 0) and post- (days 5, 8, and 12) infusion
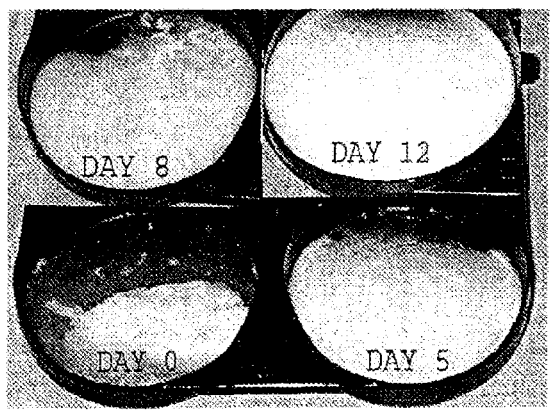
Figure 9A. Appearance of milk from Cow 264LF sampled pre- and post-infusion of *Lactococcus lactis* DPC 3147. Samples shown on Day 0 and Days 5, 8 and 12 post-infusion.
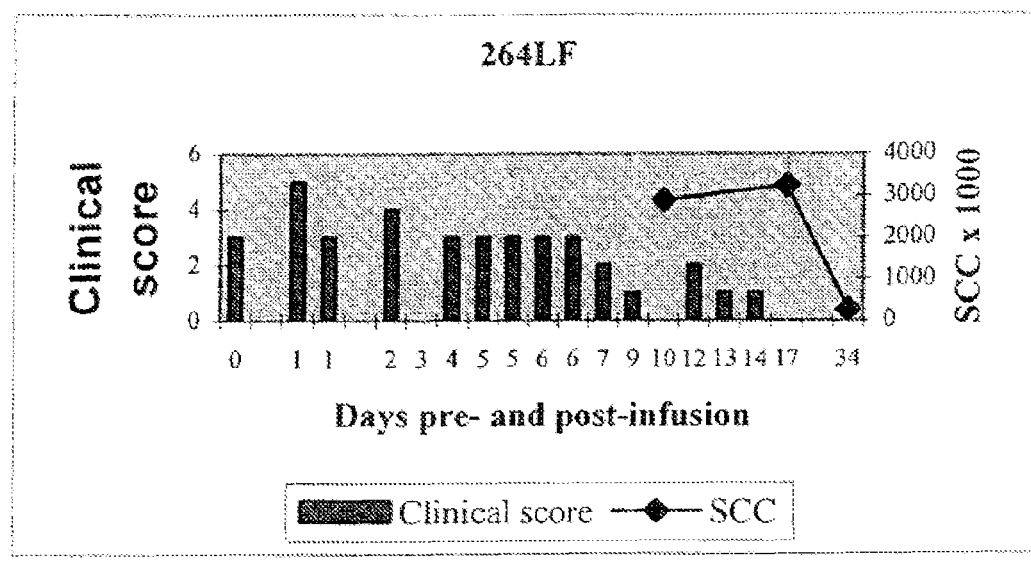
Figure 9B. Graphs of Somatic Cell Count and Clinical Score in milk from Cow 264LF sampled pre- and post-infusion of *L. lactis* DPC 3147.

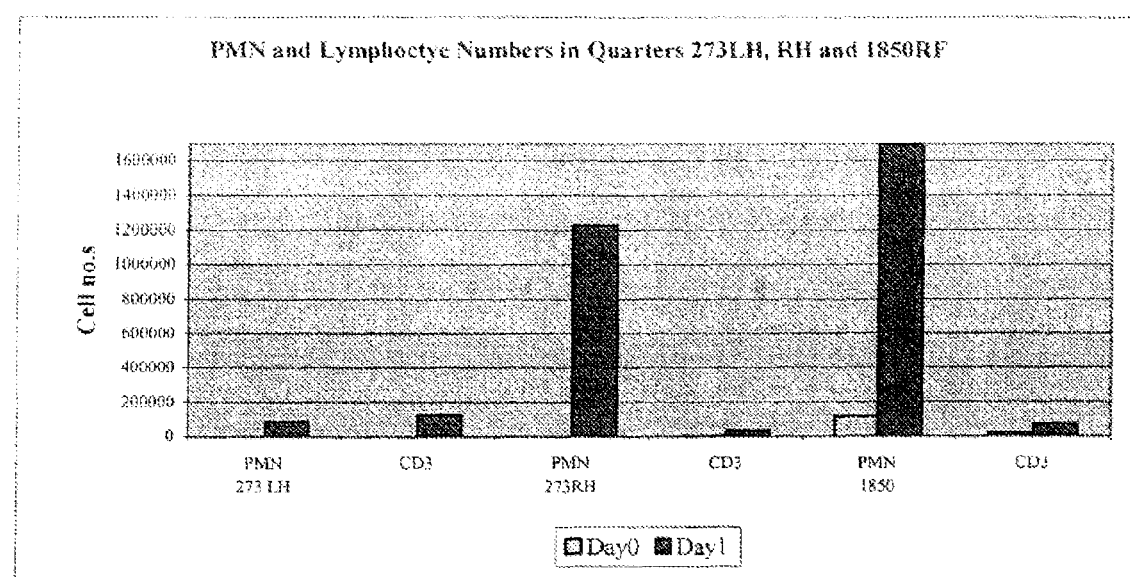
Figure 10. Leukocyte numbers in individual quarters before and after treatment with either *Lactococcus lactic* DPC3147 (Cow 273RH and Cow 1850RF); or sterile broth (Cow 273 LH).

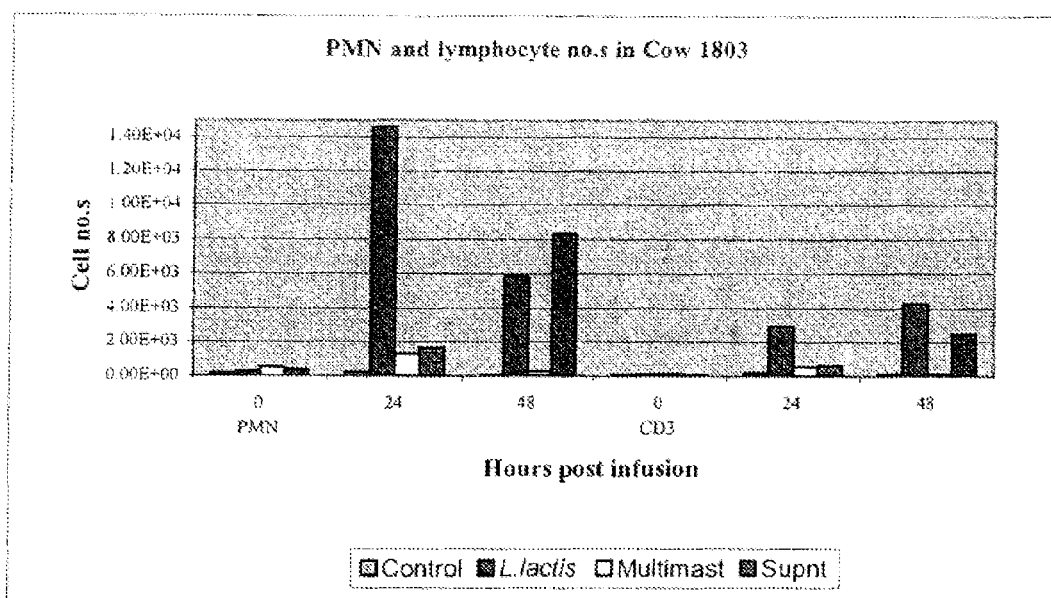
Figure 11. Leukocyte numbers in individual quarters before and after treatment with either *Lactococcus lactic* DPC3147 (RH); intra mammary antibiotic (LF); cell-free supernatant (LH) or untreated control (RF).

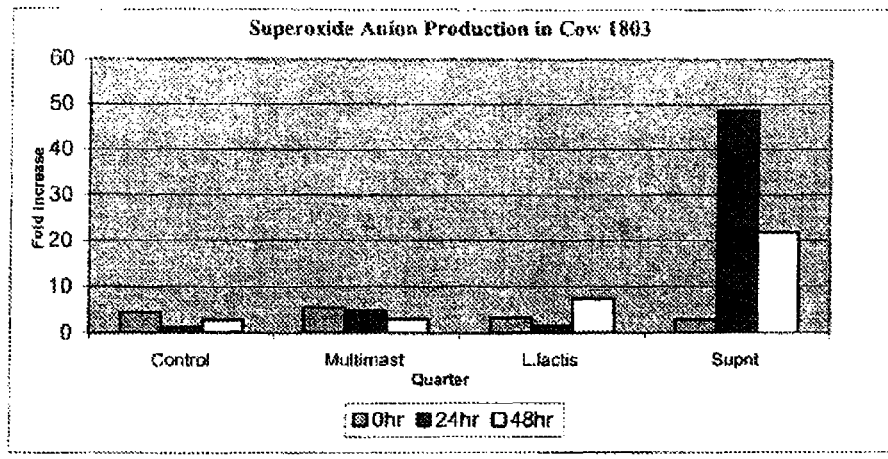

Figure 12A. Superoxide Anion Production by PMN in each of four quarters in one cow (Cow 1803) before and after treatment with either *Lactococcus lactis* DPC3147 (RH); intra-mammary antibiotic (LF); cell-free supernatant (LH) or untreated control (RF).

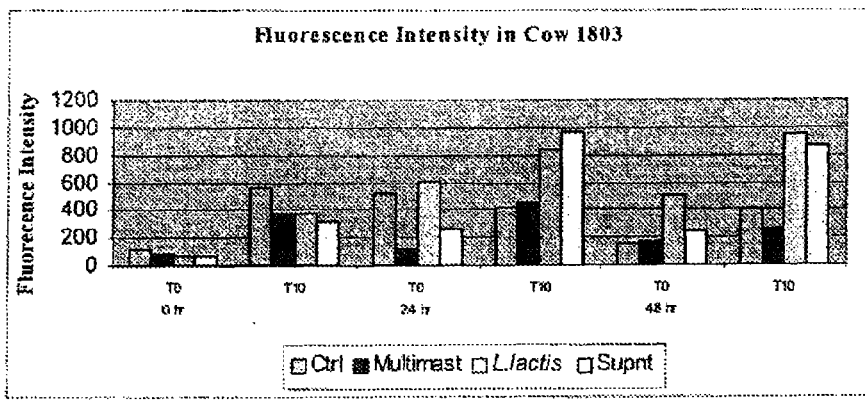

Figure 12B. Levels of superoxide anion fluorescence intensity in each of the four quarters of Cow 1803 before and after treatment with either *Lactococcus lactis* DPC3147 (RH); intra-mammary antibiotic (LF); cell-free supernatant (LH) or untreated control (RF).

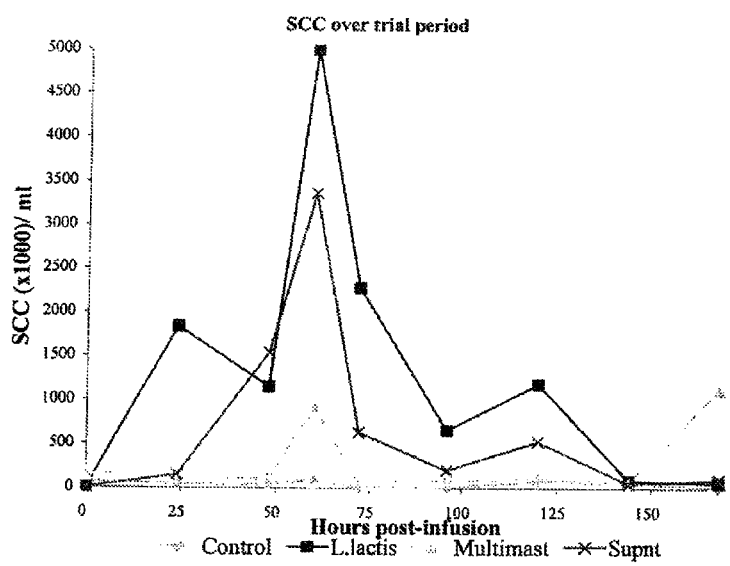
Figure 13. Somatic cell counts in the four quarters of Cow 1803 after infusion with either *L. lactis* DPC3147 (RH); intra-mammary antibiotic (LF); cell-free supernatant (LH) or untreated control (RF). Day 0 = pre-infusion.

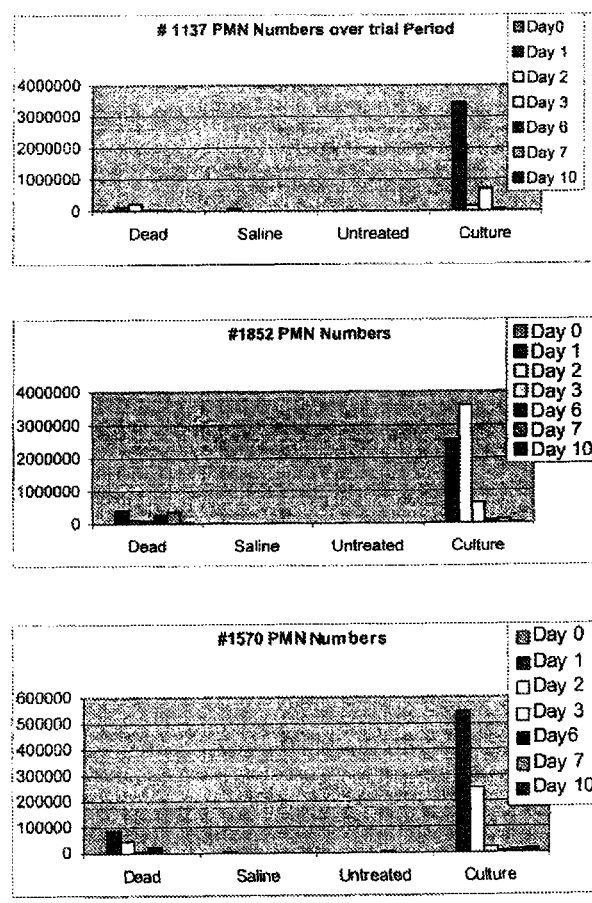
Figure 14. Leukocyte numbers in individual quarters in Cow 1137, Cow 1852 and Cow 1570 before (Day 0) and after treatment with either live *L. lactis* DPC3147, dead *L. lactis* DPC3147, sterile saline or untreated control.

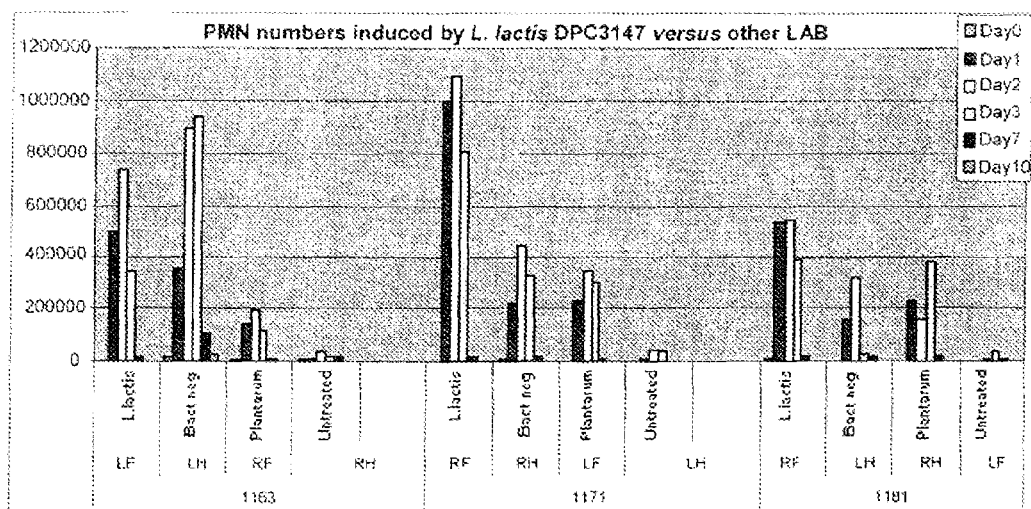
Figure 15. PMN numbers in individual quarters before and after the various treatment with either *L. lactis* DPC3147 (*L. lactis*); *L. lactis* DPC5399 (Bact neg); *Lb. plantarum* DPC4922 (plantarum) or untreated controls.

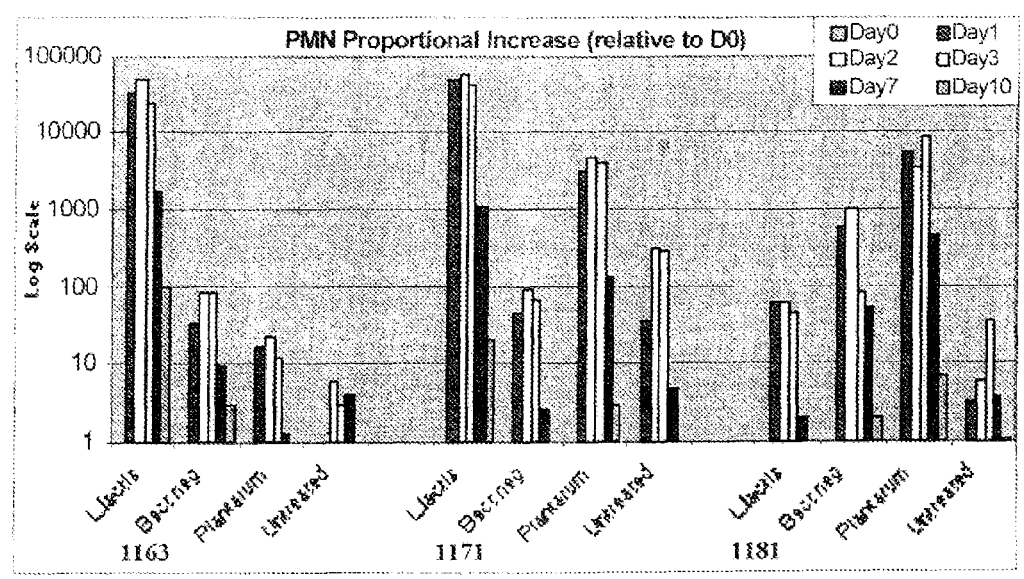
Figure 16. Relative proportional post-treatment increase in milk-derived PMN relative to pre-treatment in Cow 1163, Cow 1171 and Cow 1181 respectively.
(Note: Log scale on y-axis)

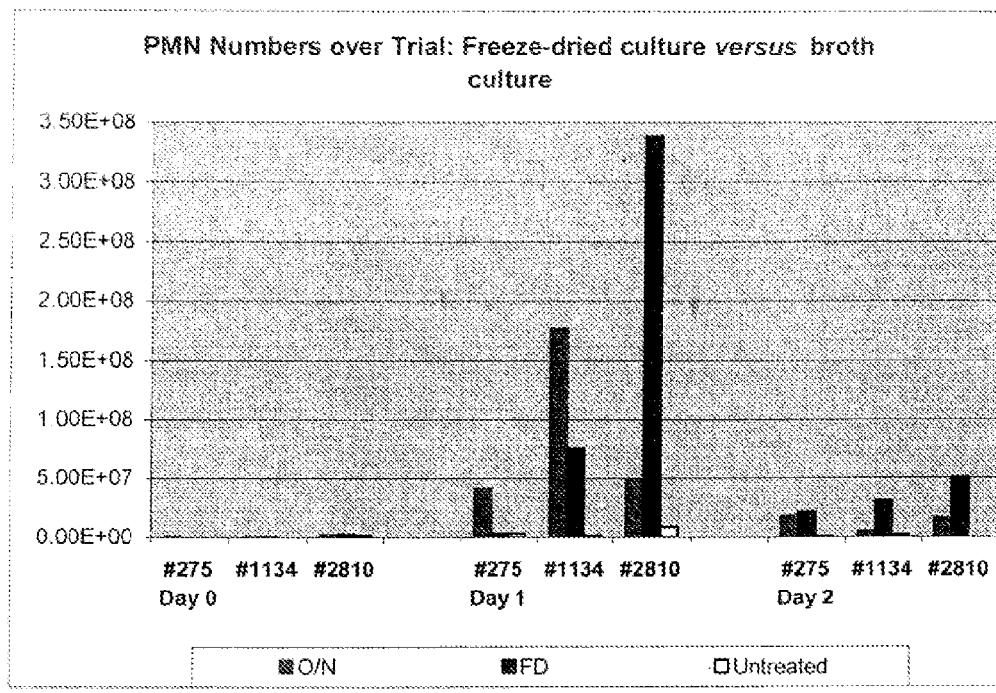
Figure 17. The effect of infusing different preparations of *L. lactis* DPC3147 on PMN numbers from Cow 275, Cow 1134 and Cow 2810. Quarters of each cow were treated with an overnight culture of *L. lactis* DPC3147 (O/N); a freeze-dried culture of *L. lactis* DPC3147 (FD) or left untreated. PMN numbers were then analysed from each quarter over two days.

USE OF PROBIOTIC BACTERIA IN THE TREATMENT OF INFECTION

FIELD OF THE INVENTION

The present invention relates to the use of live cultures of non-pathogenic, probiotic bacteria or supernatants of such cultures in the treatment of bacterial infections, particularly localised infections. In particular the invention relates to the use of live cultures of *Lactococcus lactis* or the supernatant from such cultures in the treatment of mastitis. This invention concerns the exploitation of food-grade "harmless" probiotic bacteria for the treatment of infectious diseases (or localised infections) in humans and animals. In particular the treatment involves the application of a non-pathogenic lactic acid bacterium to the infected animal/human which results in relief in clinical symptoms of the infection/disease.

BACKGROUND TO THE INVENTION

The notion of "friendly" bacteria contributing to good health and well-being was first proposed almost a century ago by Prof. E. Metchnikoff, but it is only in the last two decades that the potential health promoting role of some bacteria has been fully appreciated. Probiotic therapy uses bacterial interference and immunomodulation in the control of several infectious, inflammatory, and immunologic conditions. For instance, there is growing evidence to suggest that while an impoverished or absent gastrointestinal (GI) tract microflora can lead to digestive problems like hypoallergenic intolerance; recolonisation by "friendly" bacteria has the capacity to restore oral tolerance and regain the development of a balanced immune system (Alvarez-Olmos and Oberhelman, 2001; Cross, 2002). While the intricacies of signalling between the de novo colonisers and the immune system are not fully elucidated, it is believed that modulation of the immune response probably occurs through one or a combination of the following mechanisms (Cross, 2002):
1. Localised lactic acid production by probiotics, which may limit the growth of pathogens.
2. Production of anti-pathogenic substances by the probiotic strain e.g. bacteriocins, which are potent bactericidal compounds.
3. Limitation of colonisation by competing for colonisation sites-"competitive exclusion".
4. Production of immunomodulatory signals by the probiotic strain that stimulate the host immunity sufficiently to afford a degree of enhanced protection.

Lactic acid bacteria (LAB), including members of the genera *Lactococcus, Lactobacillus, Leuconostoc, Pedicococcus* and *Streptococcus* have been used for millennia in the production of fermented foods. As a result of their history as harmless bacteria, these microorganisms are considered as GRAS (Generally Regarded As Safe) for many applications, including human and animal consumption. In recent years, there has been extensive research into the use of LAB in the control of pathogenic microorganisms, and as health-promoting agents or "probiotics".

To date, probiotic therapy has mainly been exploited in the treatment of gastrointestinal problems. While initially based on hearsay and tradition, the peer-approved scientific evidence now supporting the protective role of probiotics and in particular the LAB lactobacilli, in the GI tract is immense. Multiple antimicrobial properties of probiotics have been suggested as potential protective factors in the human digestive system against microorganisms such as *Escherichia coli, Helicobacter pylori, Salmonella* and *Listeria* species (Alvarez-Olmos and Oberhelman, 2001). For instance, mice which were fed *Lactobacillus acidophilus, Lb. casei* or a combination of both, prior to oral challenge with *Salmonella typhimurium*, had reduced pathogen translocation to the spleen and liver, compared with control mice. This resulted in increased survival of mice in the probiotic-fed groups, particularly in the group fed both strains. This study also demonstrated that in the probiotic-fed groups, macrophages had increased phagocytic activity (Perdigon et al., 1990a).

The protective effect of *Lb. casei* against *S. typhimurium, E. coli* and *Shigella sonnei* has also been investigated in mice. Increased protection from oral challenge with the aforementioned pathogens was observed when mice were pre-fed *Lb. casei*. Additionally, increased IgA levels were observed, and probiotic-fed mice challenged with *Shigella* had increased anti-*Shigella* antibody titres in the serum and GI tract compared to the control group (Perdigon et al., 1990b; 1991).

A growing body of evidence, therefore, links increased anti-microbial protection with the enhancement of appropriate immune responses by probiotics. Recently, research has investigated the use of immunomodulatory probiotics as protective agents in the GI tract, and also at other mucosal surfaces. In one such study, mice pre-fed *Lb. casei* were subjected to an aerosolised challenge of *Pseudomonas aeruginosa* (Alvarez et al., 2001). The results demonstrated that probiotic feeding increased the clearance rate of *P. aeruginosa* from the lungs, up-regulated the phagocytic capacity of the alveolar macrophages and increased the levels of IgA in the serum and broncho-alveolar lavage fluid. It is apparent from these results that probiotic feeding can influence immuno-responses in the respiratory tract tissues and that this effect is sufficient to afford protection against bacterial respiratory tract pathogens. Furthermore, *Lb. rhamnosus* GR-1 and *Lb. fermentum* RC-14 are well recognised as therapeutic agents in the prevention and treatment of urogenital infections in women. Restoration of a healthy and normal vaginal flora occurs following local application of lactobacilli, demonstrating that probiotics delivered locally, as well as those delivered by the oral route, can provide enhanced protection against pathogens (Reid et al., 2001; Gardiner et al., 2002). Thus, the areas of potential use of probiotics has expanded rapidly in recent decades, and now includes prevention and treatment of diarrhoeal diseases in adults and children, prevention of vaginitis and urinary tract infection in adults, food allergy prevention, and antitumor action in the gut, bladder and cervix (Cross, 2002).

Apart from the obvious benefits of using GRAS organisms for the latter purposes, using Gram-positive bacteria like lactococci, lactobacilli and streptococci has the added advantage that the cell wall of Gram-positive bacteria has been shown to act as an immune-response activator. Another major attraction of using lactic acid bacteria as therapeutic agents stems from their ability to produce bacteriocins, potent anti-microbial peptides (Ross et al., 1999). These peptides kill other microorganisms rapidly by destroying or permeating the microbial membrane and impairing the ability to carry out metabolic processes. Because of their mode of action, these peptides are unlikely to face the same antimicrobial resistance mechanisms that limit current antibiotic use.

Nisin was the first identified bacteriocin derived from fermentation of a lactic acid bacterium, *Lactococcus lactis*. It is approved for use as a food preservative in the United States, and was awarded GRAS status in the U.S. Federal Register in 1988. It is also approved as a natural food preservative by more than 40 other countries as well as the World Health Organisation and the European Union. In addition to its use as a food additive to inhibit spoilage organisms and pathogens, several studies have investigated its use as a therapeutic agent, in the treatment of such diverse diseases as acne, human gastrointestinal infections and bovine mastitis (Blackburn et al., 1994; Sears et al., 1995). It is currently used as a component of a commercial teat-dip product (CONSEPT®, Babson Bros.).

Lacticin 3147 is a broad-host range bacteriocin also produced from a lactococcal strain, *L. lactis* DPC3147. It was first identified in an isolate obtained from an Irish kefir-like grain that had been used domestically for the production of buttermilk. It kills all Gram-positive bacteria tested to date, including high profile antibiotic resistant pathogens such as methicillin resistant staphylococci, vancomycin resistant enterococci, and penicillin resistant pneumococci (Galvin et al., 1999) in addition to food poisoning organisms such as *Listeria monocytogenes* and *Clostridium botulinum* (Ross et al., 1999). Similar to nisin, it is a member of the family of bacteriocins termed lantibiotics. It is a two-component bacteriocin, with both components required for full activity. Its mode of action involves the formation of pores which, by damaging the membrane of sensitive cells, leak potassium and phosphate ions. Importantly, lacticin 3147 has advantages over nisin as a choice of therapeutic agent, including its effectiveness over a broad pH range (nisin is most effective at acid pH), which suggests additional possibilities in non-acid foods and in biomedical applications (Ross et al., 1999). Lacticin 3147 has already been exploited for a wide range of applications, including use as a powdered biopreservative (Morgan et al., 1999) and in the treatment of bovine mastitis (Ryan et al., 1999; Twomey et al., 2000).

Nutritional competition is established as an important mechanism by which probiotics exert their effect. Suppressive factors such as bacteriocins and toxicity of end metabolic products have also been implicated (Alvarez-Olmos and Oberhelman, 2001; Cross, 2002).

Mastitis is defined as inflammation of the udder and is indicated by increases in Somatic Cell Count (SCC). The SCC is an indication of the levels of neutrophils in the milk, which in turn is an indication of the presence of infection. A normal udder quarter is free from pathogenic bacteria, has very few neutrophils in the milk, and thus, a low SCC ($<0.2\times10^6$/ml SCC). A rise in SCC usually indicates the presence of an infection.

When a cow has clinical mastitis, the affected quarter may have obvious signs of inflammation-heat, pain and swelling, and the cow may have an elevated body temperature. The SCC is raised above $0.2\times10^6$/ml and pathogens may (specific clinical) or may not (non-specific clinical) be detectable. Quarters are also considered clinical, if the milk is visibly abnormal—e.g. clots present, even though there may be no clinical signs on palpation. Clinical mastitis can be classified on the basis of the appearance of the milk from affected quarters. A clinical or subclinical infection is referred to as "Chronic" if it has persisted over a long period and does not respond to antibiotic treatment. Clinical chronic cases are easily identified by the milker. In subclinical cases, the affected udder appears normal but the milk has an elevated SCC ($>0.2\times10^6$/ml) and pathogens are usually present in the milk. Subclinical chronics are only identified by repeated sampling and laboratory analysis. An EC Council Directive sets out regulations for the hygienic production of milk and dairy products.

Acute and chronic cases are treated routinely with antibiotics. There are cases, however, that do not respond to antibiotic treatment, or cases which respond briefly, and then re-occur, even following repeat administration of antibiotic. Repeated antibiotic administration results in milk loss, as milk must be withheld from the creamery until the milk is free of antibiotic residues.

We have investigated the use of a live culture of *L. lactis* 3147 in the treatment of bovine mastitis. Use of the bacteriocin-producing culture in place of a concentrated lacticin preparation has certain advantages. Firstly, the producing organism, *L. lactis* is GRAS, and was isolated from a food source. The use of the live culture for the treatment of mastitis, can be viewed as a prolonged assault on the pathogen—not only is bacteriocin produced in a natural and stable manner, but the culture should also compete with pathogens for colonisation of the teat. Additionally, other antimicrobial substances, such as organic acids, free fatty acids, ammonia, and hydrogen peroxide may also be produced as end products of metabolism. Lastly, the infusion of *L. lactis* 3147 into the teat duct resulted in an immunomodulatory effect, characterised by a short-lived rise in SCC, with a concomitant reduction or elimination of pathogens; followed by a dramatic improvement in both the clinical outcome and the appearance and the quality of the milk.

OBJECT OF THE INVENTION

It is an object of the invention to provide an improved method of combating infectious diseases, particularly localised infections such as mastitis. It is a further object to provide a pharmaceutical composition or a method of treatment for such infection which does not involve the use of antibiotics and which utilises the properties of non-pathogenic and food grade bacteria.

SUMMARY OF THE INVENTION

According to the present invention there is provided use of a live culture of a non-pathogenic food-grade probiotic bacterium in the treatment of infectious diseases. The infectious disease may be a localised infection of the skin, including an infected wound, a urinary tract infection or mastitis.

The probiotic bacterium may be a non-pathogenic lactic acid bacterium. The lactic acid bacterium may be a *Lactococcus* strain. One suitable *Lactococcus* strain is *Lactococcus lactis* DPC3147.

In an alternative embodiment the invention also provides the use of the supernatant of a live culture of a non-pathogenic food-grade probiotic bacterium in the treatment of infectious disease. The disease and the bacterium may be as described above.

The invention also provides the use of a live culture of a non-pathogenic food grade probiotic bacterium or the supernatant of a live culture of a non-pathogenic food-grade probiotic bacterium in the preparation of a medicament for the treatment of infectious diseases of humans and animals.

In a still further embodiment the invention provides a pharmaceutical composition comprising a pharmaceutically effective amount of a non-pathogenic live culture of a food-grade probiotic bacterium or a pharmaceutically effective amount of the supernatant of a live culture of a non-pathogenic food-grade probiotic bacterium together with a pharmaceutically acceptable carrier or diluent.

Also provided is a method of treatment of infectious diseases comprising administering to a subject a pharmaceutically effective amount of a non-pathogenic live culture of a food-grade probiotic bacterium or the supernatant of a non-pathogenic live culture of a food-grade probiotic bacterium. The method is suitable for the treatment of mastitis.

It could not be predicted that these live cultures would be effective in disease treatment for many reasons. Firstly, in most probiotic applications the organism used is one which is normally found at the site of treatment, and most such applications are for the treatment of gastrointestinal tract problems. The effectiveness of *L. lactis* is particularly surprising in that it is not an enteric organism and moreover it is not found normally in the udder. Furthermore there has never been a suggestion in the prior art that non-pathogens could be successfully used to stimulate the immune system for these applications.

In another embodiment the invention provides use of a live culture of a non-pathogenic food-grade probiotic bacterium or the supernatant of a live culture of a non-pathogenic food-grade probiotic bacterium in a method of stimulation of the immune system for these applications.

In a further embodiment the invention provides a method of accelerating improvement in the quality of milk from cows with mastitis whereby the status of Somatic Cell Count and Total Bacterial Pathogen Count is rapidly brought within the range set by the EC Council Directive Regulations.

BRIEF DESCRIPTION OF THE DRAWINGS

FIGS. 1A and B: Somatic Cell Count values and bacterial counts in quarters of treated animals.

FIG. 2A. Appearance of milk from Cow 1154LF sampled pre- and post-infusion of *Lactococcus lactis* DPC 3147.

FIG. 2B. Graphs of Somatic Cell Count and Clinical Score in milk from Cow 1154LF sampled pre- and post-infusion of *L. lactis* DPC 3147.

FIG. 3A. Appearance of milk from Cow 1178LH sampled pre- and post-infusion of *Lactococcus lactis* DPC 3147.

FIG. 3B. Graphs of Somatic Cell Count and Clinical Score in milk from Cow 1178LH sampled pre- and post-infusion of *L. lactis* DPC 3147.

FIG. 4A. Appearance of milk from Cow 1850RF sampled pre- and post-infusion of *Lactococcus lactis* DPC 3147. Samples shown on Day 0 and 9 days post-infusion.

FIG. 4B. Graphs of Somatic Cell Count and Clinical Score in milk from Cow 1850RF sampled pre- and post-infusion of *L. lactis* DPC 3147.

FIG. 5A. Appearance of milk from Cow 1163RH sampled pre- and post-infusion of *Lactococcus lactis* DPC 3147.

FIG. 5B. Graphs of Somatic Cell Count and Clinical Score in milk from Cow 1163RH sampled pre- and post-infusion of *L. lactis* DPC 3147.

FIG. 6A. Appearance of milk from Cow 1184RF sampled pre- and post-infusion of *Lactococcus lactis* DPC 3147.

FIG. 6B. Graphs of Somatic Cell Count and Clinical Score in milk from Cow 1184RF sampled pre- and post-infusion of *L. lactis* DPC 3147.

FIG. 7A. Appearance of milk from Cow 14LH sampled pre- and post-infusion of *Lactococcus lactis* DPC 3147.

FIG. 7B. Graphs of Somatic Cell Count and Clinical Score in milk from Cow 14LH sampled pre- and post-infusion of *L. lactis* DPC 3147.

FIG. 8A. Appearance of milk from Cow 717RF sampled pre- and post-infusion of *Lactococcus lactis* DPC 3147.

FIG. 8B. Graphs of Somatic Cell Count and Clinical Score in milk from Cow 717RF sampled pre- and post-infusion of *L. lactis* DPC 3147.

FIG. 9A. Appearance of milk from Cow 264LF sampled pre- and post-infusion of *Lactococcus lactis* DPC 3147.

FIG. 9B. Graphs of Somatic Cell Count and Clinical Score in milk from Cow 264LF sampled pre- and post-infusion of *L. lactis* DPC 3147.

FIG. 10. PMN and lymphocyte numbers in individual quarters before and after treatment with either *L. lactis* DPC3147 (Cow 273RH and Cow 1850RF); or sterile broth (Cow 273 LH).

FIG. 11. PMN and lymphocyte numbers in individual quarters in Cow 1803 before and after treatment with either *L. lactis* DPC3147 (RH); intra-mammary antibiotic (LF); cell-free supernatant (LH) or untreated control (RF).

FIG. 12A. Superoxide Anion Production by PMN in each of four quarters in one cow (Cow 1803) before and after treatment with either *Lactococcus lactis* DPC3147 (RH); intra-mammary antibiotic (LF); cell-free supernatant (H) or untreated control (RF).

FIG. 12B. Levels of superoxide anion fluorescence intensity in each of the four quarters of Cow 1803 before and after treatment with either *L. lactis* DPC3147 (RH); intra-mammary antibiotic (IF); cell-free supernatant (LH) or untreated control (RF).

FIG. 13. Somatic cell counts in the four quarters of Cow 1803 after infusion with either *L. lactis* DPC3147 (RH); intra-mammary antibiotic (LF); cell-free supernatant (LH) or untreated control (RF). Day 0=pre-infusion.

FIG. 14. PMN numbers in individual quarters in Cow 1137, Cow 1852 and Cow 1570 before (Day 0) and after treatment with either live *L. lactis* DPC3147, dead *L. lactis* DPC3147, sterile saline or untreated control.

FIG. 15. PMN numbers in individual quarters before and after treatment with either *L. lactis* DPC3147 (*L. lactis*); *L. lactis* DPC5399 (Bact neg); *Lb. plantarum* DPC4922 (*plantarum*) or untreated controls.

FIG. 16. Relative proportional post-treatment increase in milk-derived PMN relative to pre-treatment in Cow 1163, Cow 1171 and Cow 1181 respectively.

FIG. 17. The effect of infusing different preparations of *L. lactis* DPC3147 on PMN numbers from Cow 275, Cow 1134 and Cow 2810. Quarters of each cow were treated with either an overnight culture of *L. lactis* DPC3147 (O/N); a freeze-dried culture of *L. lactis* DPC3147 (FD) or left untreated. PMN numbers were then analysed from each quarter over two days.

DETAILED DESCRIPTION OF THE INVENTION

Materials and Methods
Preparation of Infusion Mixture

*Lactococcus lactis* DPC3147 was isolated previously from a kefir grain. It was routinely propagated at 30° C. in M17 broth (Difco Laboratories, Detroit, USA) supplemented with 0.5% glucose or lactose. This culture (3 ml, ~$10^9$ cfu ml$^{-1}$) was either used directly, or an infusion mixture was prepared in the following way: 2 ml of an overnight culture of *L. lactis* DPC3147 were mixed with 3 ml sterile water for injection (Antigen Pharmaceuticals) to produce a working culture concentration of approximately $10^9$ cfu ml$^{-1}$. Control infusion mixtures included uninoculated broth, incubated overnight at 30° C. and then diluted in a similar fashion to the culture.

Infusion Techniques

The diluted *L. lactis* DPC3147 cultures were infused directly into the teat sinus via the streak canal. The culture was inoculated to a depth of 17 mm using a syringe with a blunted smoothed tip to prevent injury to the teat. Infusion of the mixture was usually performed after the evening milking. For the six chronic disease cases, a single application of 3 mls of undiluted culture was performed. For the nine clinical mastitis cases, infusion was performed twice at a 24 h interval for seven quarters (Cow 1163RH, 14LH, 717RF, 1154LF, 1850RF, 1184RF, 1176LH), twice with a 72 h interval for one quarter (1178LH) and four times for Cow 264LF, with 24 h between and first and second infusions, 84 h between the second and third infusion and 48 h between the third and fourth infusions (Appendix 1-9). 5 ml of the infusion mixture prepared as described above were used when infusing the quarters with clinical mastitis.

Selection of Cows for Treatment

Before in vivo experiments commenced, foremilk quarter samples were collected in an aseptic manner from all prospective cows and these were screened for mastitis-causing pathogens by streaking 10 µl on separate quadrants on the surface of ABA plates and incubating for 16 h at 37° C. Somatic cell counts (SCC) or CMT results were also determined for each quarter before treatment. Previous history of infection was also considered during selection. Six udder quarters from 4 cows with a history of chronic infection were initially selected for treatment. Nine quarters from 9 cows with newly acquired clinical infections were also treated subsequently.

Bacterial Enumeration

Eighteen hours post-infusion, foremilk samples were taken in an aseptic manner for microbiological analysis from all of the treated quarters. One hundred microlitres of each milk sample was streaked on the surface of an Aesculin blood agar plate (ABA) containing blood agar base No. 2 (Oxoid), supplemented with 7% citrated whole calf blood and 0.1% aesculin (Sigma, St. Louis, Mo., USA) and incubated for 24 h at 37° C. Following incubation, colonies were enumerated and identified on the basis of haemolytic activity and colony appearance on ABA. One hundred microlitres of each milk sample was also streaked on the surface of a M17 agar plate supplemented with 0.5% glucose or lactose and incubated overnight at 30° C.

Assay for Bacteriocin Activity

The antimicrobial activity of *L. lactis* colonies was assessed against *L. lactis* HP, using the agar well diffusion assay described previously (Parente and Hill, 1992). Additionally, colonies isolated on GM17 or LM17 from milk were selected randomly, purified and assayed to confirm isolation of *L. lactis* DPC3147 from udder quarters.

Immunological Studies

Two independent studies were performed to investigate the effect of *L. lactis* DPC 3147 on the immunity of the cow. In the first study, two cows were used, an uninfected animal (Cow 273) and an infected animal with high SCC (Cow 1850). One quarter of Cow 273 was infused with sterile broth as a control (Left Hind, LH) and one quarter was infused with the *L. lactis* culture (Right Hind, RH). One quarter of Cow 1850 was also infused with the *L. lactis* culture (RF). Milk samples were taken immediately prior to intramammary infusion (Day 0) to determine baseline levels of leukocyte subpopulations. Milk samples were also collected 16 hours following treatment (Day 1). In a second study, an infection-free cow with SCC counts in all udder quarters of <100,000/ml was chosen for immunological studies. One quarter (RH) was inoculated with the *L. lactis* DPC3147 preparation, a second quarter (LH) was infused with cell-free supernatant from an overnight culture of *L. lactis* DPC3147, a third quarter (LF) was infused with the contents of one intra-mammary antibiotic syringe containing 250 mg of Neomycin Sulphate, 100 mg of Procaine Penicillin, 10 mg of Oxytetracycline Hydrochloride and 10 mg of Prednisolone (Multimast L.C., Bimeda Ltd., Dublin) and one quarter (RF) was left untreated. Milk samples were taken just prior to intra-mammary injections (Day 0) and also at 24 and 48 hours following treatment. All samples from both trials were stored at room temperature following milking and were analysed within three hours of collection. Neutrophils and lymphocytes were identified using a combination of bovine-specific antibodies (BN15.6 and CD3 respectively) and precise gating techniques in flow cytometry. Superoxide anion production assays were performed to assess the functional activity of neutrophils. In the second trial, milk samples were also taken every 24 h for up to 7 days to monitor the Somatic Cell Count (SCC).

Effect of Using Dead Cells

An experiment was performed to investigate the effect of infusing dead *L. lactis* DPC3147 cells on the immune response of cows. Three low SCC cows were selected (Cow 1852, 1135, and 1570) and the teats were randomised and infused with either live lactococci, dead lactococci or sterile saline (0.85% NaCl {w/v}). The live lactococci infusion mixtures were prepared as described above. Dead cells were prepared by growing *L. lactis* DPC3147 in LM17 overnight as described above, followed by boiling at 100° C. for 10 min. Following boiling, the bacteria were plated on LM17 agar and incubated overnight to confirm lack of viability. The dead culture was mixed with sterile water for injection in a ratio of 2:3, and this mixture was used for infusion as described above. Similarly, sterile saline was also mixed with sterile water for injection and infused as a control. A fourth quarter was left untreated in each cow as a negative control. Milk samples were taken just prior to intra-mammary injections (Day 0) and on Days 1, 3, 6, 7 and 10 following treatment. All samples were then analysed for immunological activity as described above.

Effect of Using Other Lactic Acid Bacteria

*Lactobacillus plantarum* DPC4922 was grown anaerobically at 37° C. in MRS medium. *L. lactis* DPC5329, a derivative of *L. lactis* DPC3147, which is incapable of producing bacteriocin (Bac-), was grown in an identical manner to *L. lactis* DPC3147 (as described above). Three cows (Cow 1163, Cow 1171 and Cow 1181) were selected to investigate the effects of infusing potential probiotic bacterial strains on the immune response of the mammary gland of cows with low somatic cell counts. Three cows were used to monitor the immune responses amongst different animals. Each quarter received a different treatment, with the treatments randomised amongst teats.

Milk samples were taken just prior to intramammary injections (Day 0), to determine baseline levels of leukocyte subpopulations. Milk samples were also collected 1, 2, 3, 7 and 10 days following treatment. All samples were stored at room temperature following milking and were analysed within three hours of collection. Neutrophils and lymphocytes were identified using a combination of bovine-specific antibodies and flow cytometry.

Preparation of Freeze Dried *L. lactis* DPC 3147.

LM17 (200 ml) was inoculated with 1% (v/v) *L. lactis* DPC3147 and incubated overnight at 30° C. The cells were then harvested by centrifugation at 4° C. and 4500 rpm in a Sorvall RC 3Cplus centrifuge. The supernatant was removed and the cells were resuspended in ~150 ml sterile distilled water. The cells were then harvested again by centrifugation and the pellet was resuspended in ~100 ml sterile distilled water. The resuspended cells were then freeze-dried to a powder preparation overnight using a Modulyo Freeze Dryer (Edwards). A sample of the resulting powder was then resuspended in sterile distilled water as a 10% solution and bacteria were enumerated by plating dilutions on LM17 agar and incubating overnight at 30° C. Appropriate amounts of powder were then added to 5 ml of sterile water for injection such that the final concentration was equivalent to $10^9$ cfu $ml^{-1}$ approximately. Powder resuspended in this way was then used as an infusion mixture.

Comparison of Different Preparations of *L. lactis* DPC3147

An infusion mixture containing resuspended freeze-dried *L. lactis* DPC3147 cells was prepared as described above. This mixture, and a standard infusion mixture (diluted broth culture) were then infused randomly into teats of three different cows. Three different cows were used to allow for variation between different cows in immunological response. One quarter in each cow was left untreated as a negative control. Milk samples were taken just prior to intramammary injections (Day 0), to determine baseline levels of leukocyte subpopulations. Milk samples were also collected at 24 h and 48 h following treatment. All samples were stored at room temperature following milking and were analysed within three hours of collection. Neutrophils and lymphocytes were identified as outlined above.

Comparison of *L. lactis* Treatment Using Broth Cultures with Antibiotic Therapy A small-scale trial was performed to assess the efficacy of treatment with *L. lactis* DPC3147 in comparison to a commonly used intra-mammary antibiotic containing amoxycillin (200 mg) and clavulanic acid (50 mg), (Synulox, Pfizer animal Health). 24 infected quarters in 12 cows were used, and quarters were infused with either *L. lactis* DPC3147 (285LH, 370RH, 400LH, 598LF, 1157LF, 1170LF, 1183LH, 1658RF, 1807LF, 1827RH, 1867LH, 1868LF) or Synulox (285RF, 370RF, 400RH, 598RF, 1157RF, 1157LH, 1170LH, 1183LF, 1807RH, 1807LH, 1867RH, 1868RF). The antibiotic was administered three times, at 12 hour intervals, as per the manufacturer's instructions. The *L. lactis* DPC3147 infusion mixture was administered twice, with a 24 h interval between infusions. SCC and standard microbiological analysis were performed before and after infusion, and samples were also taken 7 days post-infusion and 12 days post-infusion.

The Treatment of Clinical Mastitis Using a Resuspended Freeze-Dried Preparation of *L. lactis* DPC3147 in a Comparison with a Positive Control (Antibiotic Therapy)

This study was performed over a 6-month period. 50 cases of clinical mastitis in 48 cows were detected by farm staff during routine milking and were selected for the trial. The quarters were classified as having either mild (C1/C2 mastitis, 25 quarters) or severe (C3/C4 mastitis, 25 quarters) clinical mastitis. Quarters were treated with the antibiotic Leo Yellow Milking Cow® (Penethamate Hydriodide 150 mg, Dihydrostreptomycin 150 mg, Framycetin sulphate 5 mg, Leo Laboratories Ltd., Dublin, Ireland) or with a resuspended freeze-dried culture of *L. lactis* DPC 3147 prepared as described above. Infusions of the culture or the antibiotic were administered three times, with a 24 h interval between each infusion. Milk samples were taken on Day 1 prior to treatment and on Day 7 and Day 14 post-treatment. Pathogens were enumerated and the SCC or CMT was determined for all samples as described previously. Quarters were also assessed at every milking during the 14-Day trial period to detect any adverse effects of treatment. Analysis of the Day 14 sample allowed quarters to be classified as a "cure" or "no cure". Cured quarters were defined as having a "clinical cure" if the milk had no visible clots or flakes, and the SCC was $<9\times10^6$ cells $ml^{-1}$. The presence or absence of pathogens was not taken into account when classifying as a "clinical cure". Quarters were defined as having a "bacteriological cure" if the SCC of the Day 14 sample was $<1\times10^6$ cells $ml^{-1}$ and the pathogen count was $<0.5$ cfu $\mu l^{-1}$ in the milk sample.

Results

Treatment of Chronic Infections

Six udder quarters from 4 cows with a history of chronic infection were selected for treatment. Eighteen hours after infusing the *L. lactis* DPC3147 culture, milk samples were taken from each udder. Samples were taken at intervals up to approximately 30 days post-infusion and bacteria enumerated as described above. Colonies were identified as *L. lactis* DPC3147 by the production of lacticin 3147. Staphylococci and streptococci were identified on the basis of their characteristic haemolysis on blood agar. In three of the quarters (714RH, 714LF and 96RF), infusion of *L. lactis* DPC3147 was followed by a sharp rise in SCC, and a concomitant reduction/elimination of the pathogen (staphylococci) (FIG. 1A). In three of the quarters (714LH, 700RH and 408RH) the infection persisted despite infusion of the lactococcal culture (FIG. 1B). However, interestingly, in the latter three udder quarters, the lactococcal culture did not appear to colonise the udder quarter (FIG. 1B), whereas in the "cured" quarters, the presence of *L. lactis* DPC 3147 was evident (FIG. 1A). The lactococcal culture did not survive long-term in any of the udder quarters. Somatic cell counts returned rapidly to, and remained at acceptable levels in all quarters.

Treatment of Clinical Mastitis

The above results prompted us to investigate the effect of infusing of *L. lactis* DPC3147 into clinically affected quarters. Nine quarters from 9 cows with newly acquired clinical signs of mastitis were treated. After treatment, milk samples were collected daily for up to 14 days and intermittently for up to 55 days. Bacterial cultures were enumerated on ABA or GM17 as described above. In all cases the quality and appearance of the milk improved dramatically following the infusion of the lactococcal culture (FIGS. 2-9). In some cases, despite the clinical nature of the milk, no pathogen was cultured prior to infusion. Where a pathogen was identified, however, infusion of the *L. lactis* DPC3147 culture resulted in the elimination/reduction of the pathogen. Pathogens eliminated included *Staphylococcus epidermidis* (Cow 14 LH), *S. aureus* (Cow 1184 RF) non-haemolytic *E. coli* (Cow 1163 RH), and *Strep. uberis* (Cow 1154 LF and Cow 264 LF) (Table 1). In two cases, while treatment resulted in an improved appearance and quality in the milk, the pathogen was not eliminated. These cases included one *Strep. uberis* infection (Cow 1176LH) and one *S. aureus* infection (Cow 1850RF) (Table 1). The data from this trial, including historical data on all the cows used can be viewed in Tables 1-7 and FIG.1A and 1B.

TABLE 1

Pathogens Isolated and Milk Somatic Cell Counts Pre- and Post-Infusion

| Cow No./Qr | Pathogen isolated | Pathogens Day 0 | Pathogens post-infusion$ | Clinical score‡ Day 0 | SCC post-infusion* ×1000/ml | Final SCC$ ×1000/ml |
|---|---|---|---|---|---|---|
| 14LH | S. epidermidis | ++++ | 0 | 3 | 2500 | 237 |
| 1850RF | S. aureus | ++++ | + | 4 | 1890 | 898 |
| 1184RF | S. aureus | + | 0 | 1 | 531 | 85 |
| 1154LF | Strep. uberis | ++++ | 0 | 5 | 2585 | 333 |
| 264LF | Strep. uberis | ++++ | 0 | 3 | 3239 | 269 |
| 1176LH | Strep. uberis | ++++ | ++++ | 2 | 6354 | 5992 |
| 1163RH | Non-haemolytic E. coli | ++++ | 0 | 3 | 846 | 148 |
| 1178LH | No bacteria | 0 | 0 | 5 | 1814 | 90 |
| 717RF | No bacteria | 0 | 0 | 2 | 933 | 43 |

++++ Too numerous to count
+ = 500-1000 cful ml$^{-1}$
‡All cows were clinical. The score was evaluated from the clinical appearance of the milk, and any additional abnormalities (eg visible clots in milk). A value of 0 indicates that the milk was subclinical in which case the SCC was determined. These clinical scores were also used when graphing data.
*Cow 14LH and Cow 717 sampled at day 4, Cow 1184RF and Cow 1154LF at day 6, Cow 302RF at day 7, Cow 1163RH and Cow 1850RF at day 8, Cow 1178LH and Cow 1176LH at day 12 and Cow 264 LF at day 16.
$Cow 1154LF sampled at day 8, Cow 1184RF at day 16, Cow 1163RH at day 25, Cow 264LF at day 35, Cow 14LH and COW 717RF at day36, Cow 1850 at day 40 and Cow 1178 at day 55.

Immunological Studies

The effect of the probiotic *L. lactis* DPC3147 on the immune systems of cows was investigated by analysing leukocyte levels and phenotypes in milk. In an initial pilot trial, the effect of *L. lactis* on the immune response of two cows was investigated. Both an infected animal and an infection-free cow were used. The results (FIG. 10) indicated that infusion of the *L. lactis* DPC3147, but not the infusion of sterile broth, resulted in a massive recruitment of PMN to the udder, indicating the *L. lactis* may be a specific trigger of the mammary immune response and elicits PMN migration and accumulation. Superoxide anion production assays were also performed and indicated that the newly recruited neutrophils had a higher respiratory burst capacity than resident neutrophils, thus providing the mammary gland with an effective mechanism for the elimination of mastitis pathogens.

In light of these results, a second trial was performed. An uninfected animal (Cow 1803) was chosen to investigate the effects of the *L. lactis* culture. As controls, one quarter (LF) was infused with a lactating-cow antibiotic (Multimast L.C.) and one quarter (RF) was left untreated. A third quarter (HL) was infused with cell-free supernatant from an overnight culture of *L. lactis* DPC3147, and the final quarter (RH) was infused with the diluted *L. lactis* DPC3147 culture. Milk samples were collected pre- and post-infusion and analysed for SCC and differential cell (leukocyte) count. FIG. 11 presents neutrophil (PMN) and lymphocyte (CD3) proportions in milk samples before treatment (0 hour) and after treatment (24 and 48 hours). Actual values were calculated using the percentage of positive cells from live/dead flow cytometry analysis and results from the Bentley Somacount Somatic Cell Counter. PMN levels in the control quarter (RF) remained unchanged during the trial period. The probiotic-injected quarter (RH) experienced a dramatic increase in neutrophils over the first 24 h period from $2.85 \times 10^2$ cells/ml before treatment to $1.46 \times 10^4$ cells/ml at 24 h after treatment (FIG. 11 and Table 2). The supernatant and antibiotic treatments also induced an increase, albeit not as pronounced (from $4.29 \times 10^2$ cells/ml to $1.68 \times 10^3$ cells/ml and $5.5 \times 10^2$ to $1.3 \times 10^3$ respectively), in PMN levels in milk (Table 2). At 48 hours the PMN levels appeared to decrease in the *L. lactis* treated and in the Multimast-treated quarter, but continued to rise in the supernatant-treated quarter (Table 2). Considering these results, it can be concluded that the injection of the *L. lactis* culture resulted in a massive recruitment of PMN to the udder in the 24 hour period following treatment. The culture supernatant also induced a recruitment of PMN to the udder and this was a more sustained induction increasing over 24 hours and continuing to rise, up to 48 hours after treatment. The antibiotic Multimast generated a weaker transient recruitment of PMN to the udder. These results suggest that both the *L. lactis* culture and the culture supernatant could be specific triggers of the mammary immune system response and elicit PMN migration and accumulation. It is possible that the factor responsible for the immune response could be released into the growth medium, which would explain the significant PMN migration in response to the culture supernatant. Levels of lymphocytes were also investigated. The *L. lactis* culture, and the culture supernatant to a lesser extent, triggered an influx of lymphocytes to the udder; the antibiotic, however, did not alter the level of lymphocytes present when compared to the control values (Table 2).

TABLE 2

Levels of PMN and lymphocytes (CD3) in all udder quarters in Cow 1803 before and after each treatment over the 48-hour trial period.

| | PMN | | | CD3 | | |
|---|---|---|---|---|---|---|
| Quarter | 0 hr | 24 hr | 48 hr | 0 hr | 24 hr | 48 hr |
| Right Front (RF)[1] | 215 | 253 | 101 | 77.7 | 218 | 129 |
| Right Hind (RH)[1] | 285 | 14600 | 5850 | 108 | 2920 | 4280 |
| Left Front (LF)[1] | 551 | 1330 | 297 | 143 | 596 | 137 |
| Left Hind (LH)[1] | 429 | 1680 | 3330 | 85.1 | 651 | 2500 |

[1]Infusion mixtures were prepared as described in Materials and Methods and quarters were treated as follows: RF: untreated; RH: *L. lactis* DPC3147; LF: Antibiotic (Multimast) and LH: Cell-free supernatant.

The functional activity of PMNs in the quarter milk samples was investigated for all samples before and after injection. The results of the superoxide anion production assays are presented in FIGS. 12A and 12B. The fold increase refers to the proportional increase in superoxide anion production by PMN, from a resting state (T0) to an activated state following activation by phorbol myristate acetate (PMA; incubation for 10 minutes, {T10}). The most obvious activation occurred in the LH quarter which was treated with cell-free supernatant, with a massive activation of neutrophils at 24 hours. Surprisingly, treatment with the L. lactis culture did not result in a huge fold activation of neutrophils (FIG. 12A). This can be explained, however, by results of analysis of the fluorescence intensity of all samples (FIG. 12B). The relative fluorescence intensity is a measurement of the fluorescence emitted by the cells; a stronger fluorescence indicates a higher capacity to generate superoxide anion. The resting resident neutrophils in the L. lactis-treated quarter (T0) already possessed a very high superoxide anion production capacity (elevated fluorescence intensity) at 24 hours, and, therefore, could not exhibit a marked increase in activation following PMA treatment. In conclusion, L. lactis treatment resulted in a massive recruitment of PMN to the udder which were in a highly activated state. The Multimast treatment did not alter superoxide anion production in the treated quarter and the control quarter did not change significantly over the trial period (FIGS. 12A and 12B). The PMNs recruited in response to culture supernatant treatment also possessed an elevated superoxide anion production capacity, which appeared to peak over the first 24-hour period following treatment. The results indicated that intramammary treatment with L. lactis DPC3147 or with the cell-free supernatant generated from this culture, activated the mammary immune response by triggering the influx of neutrophils to the mammary gland (FIG. 11). These newly recruited neutrophils appeared to possess a higher respiratory burst capacity than resident neutrophils (FIG. 12).

The somatic cell count was monitored every 24 hours up to 7 days following treatment and cell counts are presented in FIG. 13 and Table 3. From FIG. 13 and Table 3, it is clear that L. lactis DPC3147 elicits an enormous cellular response by 24 hours resulting in an elevated SCC, which peaks after 48 hours resulting in a mild clinical infection and gradually drops back to normal over the course of 3-4 days. Treatment with the culture supernatant appeared to elicit a similar response. Our analysis of leukocyte populations and neutrophil activity levels confirm these findings up to 48 hours.

TABLE 3

Somatic cells counts (×1000/ml) in milk from four udder quarters assayed for immunological responses in Cow 1803.

| Days (Hours) | Right Front[a] (RF) | Right Hind[a] (RH) | Left Front[a] (LF) | Left Hind[a] (LH) |
|---|---|---|---|---|
| 0 (0)* | 66 | 1 | 158 | 7 |
| 1 (24) | 149 | 121 | 1834 | 95 |
| 2 (48) | 43 | 1150 | 99 | 1542 |
| 2 (60) | 94 | Clinical | 908 | 3360 |
| 3 (72) | 4 | 2779 | 69 | 6296 |
| 4 (96) | 9 | 656 | 81 | 202 |
| 6 (120) | 69 | 85 | 58 | 54 |

*day 0 = Time of infusion. Samples were taken daily following infusion.
[a]RF quarter was left untreated, the RH, LF and LH quarters were infused with either L. lactis DPC3147 overnight culture, the antibiotic Multimast, or cell-free culture supernatant from an overnight culture of L. lactis DPC3147.

Effects of Using Dead Cells

In order to investigate if viable L. lactis DPC3147 were required to produce the immune response generated above, infusion mixtures containing either live or dead cells were prepared and infused randomly into the teats of three cows as outlined in Table 4. Both live and dead cells generated a rise in SCC (data not shown), and, as can be seen from FIG. 14, the dead cells elicited a weak influx of both PMN in each of the cows. An increase in lymphocyte numbers was also observed (data not shown). This recruitment of PMN and lymphocytes in the quarters treated with the dead culture, however, was insignificant compared to the influx in response to the live culture. Thus, it would appear that viable L. lactis, but not a killed culture, can specifically elicit recruitment of PMN and lymphocytes to the mammary gland.

TABLE 4

Allocation of treatments amongst teats for trial investigating the ability of dead lactococci to elicit an immune response.

| Cow | Quarter | Treatment |
|---|---|---|
| 1137 | RF | Saline[1] |
| 1137 | RH | Live[2] |
| 1137 | LF | Control[3] |
| 1137 | LH | Dead[4] |
| 1852 | RF | Dead[4] |
| 1852 | RH | Saline[1] |
| 1852 | LF | Control[3] |
| 1852 | LH | Live[2] |
| 1570 | RF | Control[3] |
| 1570 | RH | Live[2] |
| 1570 | LF | Saline[1] |
| 1570 | LH | Dead[4] |

[1]Saline treatment: Quarters were infused with 2 ml sterile saline (0.85% NaCl {w/v}) plus 3 ml sterile water for injection.
[2]Live culture treatment: Quarters were infused with 2 ml overnight broth culture of L. lactis DPC3147 plus 3 ml sterile water for injection
[3]Untreated controls.
[4]Dead culture treatment: An overnight broth culture of L. lactis DPC3147 was killed by boiling for 10 mins, 2 ml of the dead culture plus 3 ml sterile water for injection were then infused into the quarters.

Effect of Using Other LAB

On analysis of results, the question arose as to whether the phenomenon of PMN recruitment was limited to L. lactis DPC3147 itself, or if other bacterial strains could also exert this effect. It was decided, therefore, to examine the effect of infusing other food-grade, non-pathogenic bacteria into the udder of lactating cows. A bacterial strain, Lb. plantarum DPC4922 was selected on the basis of its evolutionary divergence from L. lactis (quite distantly related) as well as the fact that as it was originally isolated from a food source, it can, like L. lactis DPC3147, be regarded as a GRAS organism. A third strain, L. lactis 5329 (a Bac- derivative of L. lactis DPC3147) was also used because of its close similarity to L. lactis DPC3147. The infusion mixtures were prepared as described in the Materials and Methods and the mixtures were then infused randomly into the teats of three cows as outlined in Table 5. FIGS. 15 and 16 present neutrophil (PMN) proportions in milk samples from the three cows over the 10 day trial period. Actual values were calculated using the percentage of positive cells from live/dead flow cytometry analysis and the Somacount readings. The response in the three cows was variable but a similar trend was observed in each case. PMN levels in all the untreated quarters remained relatively unchanged over the trial period (FIG. 15). Treatment with Lb. plantarum DPC4922 resulted in a slight increase in PMN in all quarters, approaching similar levels to that resulting from L. lactis DPC3147 treatment by day 3 in Cow 1181 (FIG. 15). However, the L. lactis DPC3147 response in Cow 1181 was somewhat reduced compared to the other two animals (FIG. 15).

TABLE 5

Allocation of treatments in each of the twelve quarters of three cows used to determine the effect of infusing different LAB strains on the immune response of cows

| Cow # | Quarter | Treatment |
|---|---|---|
| 1163 | RF | Lb. plantarum[1] |
|  | RH | Untreated |
|  | LF | L. lactis 3147[2] |
|  | LH | Bact neg[3] |
| 1171 | RF | L. lactis 3147[2] |
|  | RH | Bact neg[3] |
|  | LF | Lb. plantarum[1] |
|  | LH | Untreated |
| 1181 | RF | L. lactis 3147[2] |
|  | RH | Lb. plantarum[1] |
|  | LF | Untreated |
|  | LH | Bact neg[3] |

[1]Lb. plantarum treatment: 2 ml overnight culture of Lb. plantarum DPC4922 and 3 ml sterile water for injection.
[2]L. lactis DPC3147 treatment: 2 ml overnight culture of L. lactis DPC3147 and 3 ml sterile water for injection.
[3]Bact neg. treatment: 2 ml overnight culture of L. lactis DPC5329 (bacteriocin defective mutant of L. lactis DPC3147) and 3 ml sterile water for injection.

Infusion of L. lactis DPC3147 in each animal resulted in a dramatic increase in neutrophils in the first 24-hour period after treatment. The Bac- culture (L. lactis DPC5399) also induced an increase in all treated quarters, with particularly higher levels of PMN obtained in milk from Cow 1163. However, if the proportional increases in PMN relative to D0 are compared (FIG. 16), it can be seen that there is a significant proportional increase in PMN in the L. lactis DPC3147-treated quarter compared to the L. lactis DPC5399-treated quarter. The PMN influx seems to occur earlier in the L. lactis DPC3147-treated quarters (by day 1) compared to the quarters treated with L. lactis DPC5399 (Bac-) or Lb. plantarum DPC4922 (FIG. 15). In the quarters treated with the latter two treatments, a significant increase was only observed on Day 2 (FIG. 15). Thus, it appears that L. lactis DPC 3147 can elicit a stronger and more rapid immune response than either a bacteriocin negative derivative of the same strain or another LAB strain, though the latter strains may also elicit a weaker response.

Comparison of Different Preparations of L. lactis DPC3147

In order to investigate if different preparations of L. lactis DPC3147, other than the standard overnight culture (broth preparation) could produce the immune response generated above, infusion mixtures containing either freeze-dried cells, or broth cultures were prepared. The mixtures were then infused randomly into the teats of three cows as outlined in Table 6. The results (FIG. 17) show an increase in PMN by Day 1 in both treated quarters compared to the untreated quarter in each animal tested. There seems to be a greater influx in two of the overnight culture-treated quarters compared to quarters treated with the freeze-dried culture (Cow 275 and Cow 1134) with a higher number of PMN elicited by the freeze-dried culture in the remaining animal (Cow 2810). The variation in response is due to the typical variations in immune response between different animals. Thus, both "fresh" and freeze-dried preparations of L. lactis DPC3147 are capable of eliciting an immune response in the mammary gland.

TABLE 6

Treatments in each of the twelve quarters of three cows used to determine the effect of infusing different preparations of L. lactis DPC3147 on the immune response of cows.

| Cow | Quarter | Treatment |
|---|---|---|
| 275 | RF | Freeze dried culture[1] |
|  | RH | Broth culture[2] |
|  | LF | Untreated[3] |
| 1134 | RH | Freeze dried culture[1] |
|  | RF | Broth culture[2] |
|  | LF | Untreated[3] |
| 2810 | LF | Freeze dried culture[1] |
|  | RH | Broth culture[2] |
|  | RF | Untreated[3] |

[1]Freeze dried culture: The freeze-dried powder was prepared as described in Materials and Methods and resuspended in a total volume of 5 ml.
[2]Broth Culture: An overnight culture of L. lactis DPC3147 was diluted with water ad described in Materials and Methods and used as the infusion mixture.
[3]Untreated: Untreated controls quarters.

Comparison of L. lactis DPC3147 Treatment with Intra-Mammary Antibiotic Treatment The effects of using L. lactis DPC3147 treatment versus using a commonly used antibiotic treatment both for treatment and prevention of intramammary infections caused by S. aureus are shown in Table 7. As can be seen in the Table, by Day 7, the L. lactis results were very promising, with staphylococci isolated from only two quarters of the 7 quarters originally infected with this organism. In comparison, the quarters treated with Synulox were still shedding S. aureus from 6 of the 8 quarters originally infected. However, by day 12, two more of the quarters infused with L. lactis were also shedding S. aureus, giving a total of 3/7 "cured" by L. lactis treatment as opposed to 2/8 "cured" by the synulox treatment. These data indicate that the L. lactis DPC3147 treatment is as effective at eliminating infections as the Synulox treatment.

TABLE 7

Effects of using L. lactis DPC3147 treatments versus treatment with the intra-mammary antibiotic Synulox.

| | | | Day 0 | | Day 7 | | Day 12 | |
|---|---|---|---|---|---|---|---|---|
| Cow No | Qt | Treatment | SCC | S. aureus | SCC | S. aureus | SCC | S. aureus |
| 285 | LH | L. lactis 2 × 24 h 5 ml | 4759 | 0[1] | 2437 | 0 | 6138 | 0 |
| 370 | RH | L. lactis 2 × 24 h 5 ml | 5227 | +[1] | 271 | 0 | 2399 | 0 |
| 400 | LH | L. lactis 2 × 24 h 5 ml | 592 | ++[1,2] | 2892 | 0 | 1358 | 0 |
| 598 | LF | L. lactis 2 × 24 h 5 ml | 2388 | 0 | 3954 | 0 | 2697 | 2 |
| 1157 | LF | L. lactis 2 × 24 h 5 ml | 121 | 0 | 2094 | 0 | 872 | 0 |
| 1170 | LF | L. lactis 2 × 24 h 5 ml | 3690 | ++ | 1568 | ++ | 3939 | ++ |
| 1183 | LH | L. lactis 2 × 24 h 5 ml | 3638 | ++ | 859 | 0 | 138 | 0 |
| 1658 | RF | L. lactis 2 × 24 h 5 ml | 5601 | + | 3143 | 0 | 2604 | 0 |

TABLE 7-continued

Effects of using *L. lactis* DPC3147 treatments versus treatment with the intra-mammary antibiotic Synulox.

| Cow No | Qt | Treatment | Day 0 SCC | Day 0 S. aureus | Day 7 SCC | Day 7 S. aureus | Day 12 SCC | Day 12 S. aureus |
|---|---|---|---|---|---|---|---|---|
| 1807 | LF | *L. lactis* 2 × 24 h 5 ml | 390 | 0 | 2325 | 0 | 1124 | ++ |
| 1827 | RH | *L. lactis* 2 × 24 h 5 ml | 2892 | ++ | 1752 | 0 | 2998 | + |
| 1867 | LH | *L. lactis* 2 × 24 h 5 ml | 2057 | +++[1] | 1791 | +++ | 2388 | +++ |
| 1868 | LF | *L. lactis* 2 × 24 h 5 ml | 661 | 0 | 3631 | 0 | 1568 | 0 |
| 285 | RF | Synulox 3 × 12 h | 7659 | + | 2721 | + | 5318 | + |
| 370 | RF | Synulox 3 × 12 h | 761 | ++ | 209 | 0 | 406 | 0 |
| 400 | RH | Synulox 3 × 12 h | 1735 | ++ | 2001 | 0 | 1141 | 0 |
| 598 | RF | Synulox 3 × 12 h | 2160 | +++ | 2073 | +++ | 2862 | ++ |
| 1157 | RH | Synulox 3 × 12 h | 2999 | + | 2885 | ++ | 1539 | + |
| 1157 | LH | Synulox 3 × 12 h | 86 | 0 | 109 | 0 | 377 | 0 |
| 1170 | LH | Synulox 3 × 12 h | 428 | 0 | 301 | 0 | 854 | 0 |
| 1183 | LF | Synulox 3 × 12 h | 1602 | 0 | 450 | 0 | 206 | 0 |
| 1807 | RH | Synulox 3 × 12 h | 3371 | + | 3456 | 0 | 6052 | 0 |
| 1807 | LH | Synulox 3 × 12 h | 3030 | 0 | 1974 | +++ | 2730 | + |
| 1867 | RH | Synulox 3 × 12 h | 1653 | +++ | 1674 | ++ | 1885 | ++ |
| 1868 | RF | Synulox 3 × 12 h | 6684 | + | 4051 | + | 4281 | ++ |

[1]Bacteria were enumerated and scored according to the following: 0 = Absence of pathogens + = <40 cfu 10 μl-l, ++ = 40-400 cfu μl-l and +++ = >400 cfu μl-l
[2]*Streptococcus uberis* infection The Treatment of Clinical Mastitis Using a Resuspended Freeze-Dried Preparation of *L. lactis* DPC3147 in Comparison with a Positive Control (Antibiotic Therapy)

In this study, the efficacy of infusing a resuspended freeze-dried preparation of *L. lactis* DPC3147 (approximately $10^9$ cfu ml$^{-1}$) for treatment of clinical mastitis was compared to the efficacy of using an established intramammary antibiotic. Overall, 18 of the 25 cases treated with the antibiotic were defined as having a "clinical cure" on Day 14. Of these 18 quarters, nine were defined as having a "bacteriological cure"—i.e., the SCC was <1×10$^6$ cells ml$^{-1}$ and the bacteriological count was <0.5 cfu μl$^{-1}$ in the milk sample. This corresponds to an overall clinical cure rate of 72% and a bacteriological cure rate of 36% for the antibiotic treated quarters. For the quarters treated with the resuspended freeze-dried preparation of *L. lactis* DPC3147, 16 (out of 25) cases had a "clinical cure" and 7 (out of 25) cases had a "bacteriological cure". This corresponds to a clinical cure rate of 64% and a bacteriological cure rate of 28% for the probiotic-treated quarters. Comparing the two treatments, the clinical cure rate was 72% versus 64% and the bacteriological cure rate was 36% versus 28% for the antibiotic versus *L. lactis* treatments, respectively. When these values were compared using Fischer's Exact Probability Test, no statistical difference was found between treatments. This indicates that infusion of a resuspended freeze-dried preparation of *L. lactis* DPC3147 was as effective as an antibiotic in the treatment of clinical mastitis. When the treatment groups were subdivided according to the severity of the mastitis in the quarter (i.e. C1/C2 subgroups or C3/C4 subgroups) a similar trend was observed. In the C1/C2 group, 8 out of 12 cases treated with the antibiotic had a clinical cure (66.7%). Of these, 4 cases had a "bacteriological cure" (33.3%). Thirteen quarters with C1/C2 mastitis were treated with *L. lactis* DPC3147, and these quarters achieved a clinical cure rate of 76.9% and a bacteriological cure rate of 30.8%. In the C3/C4 group, 10 out of 13 cases treated with the antibiotic had a clinical cure (76.9%). Of these, 5 cases had a "bacteriological cure" (38.5%). Of the twelve quarters with C3/C4 mastitis that were treated with *L. lactis* DPC3147, 6 achieved a clinical cure (50%) and 3 were defined as having a bacteriological cure (25%). Comparison of all these values using Fischer's Exact Probability Test indicated that there was no significant difference in either the clinical or bacteriological cure rate, regardless of treatment in either the quarters with C1/C2 mastitis or the quarters with C3/C4 mastitis. Thus we can conclude that intramammary infusion of a resuspended freeze-dried preparation of *L. lactis* DPC 3147 is as effective as an intramammary antibiotic in the treatment of clinical mastitis.

CONCLUSIONS

From these results several conclusions may be drawn. Firstly, it is apparent that intramammary infusion of *L. lactis* DPC3147 into cows with chronic infections results in a rapid rise in SCC, often followed by eradication of infection. Additionally, infusion into cows with newly acquired clinical mastitis results in a rapid improvement in milk quality. *L. lactis* DPC3147 treatment has also been shown to be as effective as using a widely used commercial intra-mammary antibiotic in the treatment and prevention of intramammary infections caused by *S. aureus*. It is possible, therefore, that the infusion of *L. lactis* acts as a stimulus which induces release of proinflammatory factors and a prompt recruitment of neutrophils to the mammary gland. The results of immunological studies highlight a number of important findings that may shed some light on the mechanism of action of the probiotic bacteria *L. lactis* in the mammary gland. These findings include the following:

- Intramammary treatment with either *L. lactis* culture or the culture supernatant activates the mammary immune response by triggering the influx of neutrophils to the mammary gland.
- The *L. lactis* culture and culture supernatant appear to be specific in eliciting recruitment of PMN to the udder, when compared to the antibiotic Multimast L.C.
- These newly recruited neutrophils possess a higher respiratory burst capacity than resident neutrophils thus providing the mammary gland with an effective mechanism for the elimination of mastitis pathogens.
- The factor(s) responsible for eliciting an immune response in the udder may be a soluble factor(s) released into the growth medium, this factor(s) must be either be heat labile or destroyed/utilised rapidly when cells are killed, as dead cells plus supernatant did not elicit an immune response.
- The *L. lactis* culture must be viable to elicit an adequate immune response, although a freeze dried preparation is also effective at stimulating the immune system in the mammary gland.
- Other LAB may also be capable of eliciting an immune response in the mammary gland, in a similar fashion to L. lactis DPC 3147, though possibly not to the same extent as L. lactis DPC 3147. This implies that other LAB may also be capable of curing clinical mastitis in dairy cows and other animals if infected quarters were infused with these cultures.

Treatment with L. lactis culture or a resuspended freeze-dried preparation of L. lactis DPC3147 is as effective at eliminating infections as intra-mammary antibiotic treatment.

The words "comprises/comprising" and the words "having/including" when used herein with reference to the present invention are used to specify the presence of stated features, integers, steps or components but does not preclude the presence or addition of one or more other features, integers, steps, components or groups thereof.

REFERENCES

Alvarez, S., Herrero, C., Bru, E. and G. Perdigon (2001). Effect of Lactobacillus casei and yoghurt administration on prevention of Pseudomonas aeruginosa infection in young mice. J. Food Prot. 64:1768-1774.

Alvarez-Olmos, M. I. and R. A. Oberhelman. 2001. Probiotic agents and infectious diseases: a modern perspective on a traditional therapy. Clin. Infect. Diseases 32: 1567-1576.

Blackburn, P. Projan, S. J. and E. B. Goldberg. 1994. Pharmaceutical bacteriocin compositions and methods for doing the same. United States Patent 5: 304, 540.

Cross, M. L. 2002. Microbes versus microbes: immune signals generated by probiotic lactobacilli and their role in protection against microbial pathogens. FEMS Immun. Med. Microbiol. 1442:1-9.

Galvin, M., Hill, C. and R. P. Ross. 1999. Lacticin 3147 displays activity in buffer against Gram-positive bacterial pathogens which appear sensitive in standard plate assays. Lett. Appl. Microbiol. 28: 355-358.

Gardiner, G. E., Heinmann, C., Bruce, A. W., Beuerman, D. and G. Reid. 2002. Peristence of Lactobacillus fermentum RC-14 and Lactobacillus rhamnosus GR-1 but not L. rhamnosus GG in the human vagina as demonstrated by randomly amplified polymorphic DNA. Clin. Diagn. Lab. Immunol. 9: 92-96.

Morgan, S. M., Galvin, M., Kelly, J., Ross, R. P. and C. Hill. 1999. Development of a lacticin 3147 enriched whey powder with inhibitory activity against foodborne pathogens. J. Food Protection. 62: 1011-1016.

Parente, E., and C. Hill. (1992). Comparison of factors affecting the production of two bacteriocins from lactic acid bacteria. J. Appl. Bacteriol. 73: 290-298.

Perdigon, G., de Marcias, M. E. N., Alvarez, S., Oliver, G. and A. P. de Ruiz Holgado. 1990a. Prevention of gastrointestinal infection using immunobiological methods with milk fermented with Lactobacillus casei and Lactobacillus acidophilus. J. Dairy Res. 57: 255-264.

Perdigon, G., Alvarez, S., de Marcias, M. E. N., Roux, M. E. and A. P. de Ruiz Holgado. 1990b. The oral administration of lactic acid bacteria increases the mucosal immunity in response to enteropathogens. J. Food Protect. 53: 404-410.

Perdigon, G., Alvarez, S. and A. P. de Ruiz Holgado. 1991. Immunoadjuvant activity of oral Lactobacillus casei: influence of dose on the secretory immune response and protective capacity in intestinal infections. J. Dairy Res. 58: 485-496.

Reid, G., Beuerman, D., Heinemann, C. and A. W. Bruce. 2001. Probiotic 5 lactobacillus dose required to restore and maintain a normal vaginal flora. FEMS Immunol. Med. Microbiol. 32: 37-41.

Ross, R. P., Galvin, M., McAuliffe, O., Morgan, S., Ryan, M., Twomey, D., Meaney, W. and C. Hill. 1999. Developing applications for lactococcal bacteriocins. Antonie van Leeuenhoek 76: 337-346.

Ryan, M. P., Flynn, J., Hill, C., Ross, R. P. and W. J. Meaney. 1999. The natural food grade inhibitor, lacticin 3147 can prevent mastitis in non-lactating dairy cows. J. Dairy Sci. 82: 2625-2631.

Sears, P. M., Peele, J., Lassauzet, M., and P. Blackburn. 1995. Use of antimicrobial proteins in the treatment of bovine mastitis. In: Proceedings of the $3^{rd}$ International Mastitis seminar (p 17-18).

Twomey, D. P., Wheelock, A. I., Flynn, J., Meaney, W. J., Hill, C. and R. P. Ross. 2000. Protection against Staphylococcus aureus mastitis in dairy cows using a bismuth-based teat seal containing the bacteriocin, lacticin 3147. J. Dairy Sci. 83: 1981-1988.

The invention claimed is:

1. A pharmaceutical composition adapted for application to localised infection of the skin, comprising an anti-mastitic and immunomodulating pharmaceutically effective amount of a non-pathogenic live culture of a food-grade probiotic bacterium Lactococcus lactis strain NCIMB 40716 together with a pharmaceutically acceptable carrier or diluent.

2. The pharmaceutical composition according to claim 1, wherein the pharmaceutical composition is an infusion mixture of said strain.

3. A method of treating a subject having or at risk of developing mastitis comprising administering to a localised infection of the skin of a subject an anti-mastitic and immunomodulating pharmaceutically effective amount of a non-pathogenic live culture of a food-grade probiotic bacterium Lactococcus lactis strain NCIMB 40716 together with a pharmaceutically acceptable carrier or diluent.

* * * * *